(12) United States Patent
Papisov

(10) Patent No.: US 8,247,383 B2
(45) Date of Patent: *Aug. 21, 2012

(54) DRUG-CARRIER COMPLEXES AND METHODS OF USE THEREOF

(75) Inventor: Mikhail I. Papisov, Winchester, MA (US)

(73) Assignee: The General Hospital Corporation, Boston, MA (US)

(*) Notice: Subject to any disclaimer, the term of this patent is extended or adjusted under 35 U.S.C. 154(b) by 527 days.

This patent is subject to a terminal disclaimer.

(21) Appl. No.: 10/994,213

(22) Filed: Nov. 19, 2004

(65) Prior Publication Data

US 2006/0019911 A1    Jan. 26, 2006

Related U.S. Application Data

(63) Continuation of application No. 09/634,320, filed on Aug. 9, 2000, now Pat. No. 6,822,086.

(60) Provisional application No. 60/147,919, filed on Aug. 9, 1999.

(51) Int. Cl.
*C12N 15/11* (2006.01)

(52) U.S. Cl. .................................................. 514/44 A

(58) Field of Classification Search .................. 514/44 A
See application file for complete search history.

(56) References Cited

U.S. PATENT DOCUMENTS

| | | | |
|---|---|---|---|
| 5,478,563 A * | 12/1995 | Erami | 424/409 |
| 5,574,142 A | 11/1996 | Meyer, Jr. et al. | |
| 5,578,709 A | 11/1996 | Woiszwillo | |
| 5,624,803 A * | 4/1997 | Noonberg et al. | 435/6 |
| 5,817,343 A | 10/1998 | Burke | |
| 5,981,719 A | 11/1999 | Woiszwillo et al. | |
| 6,057,431 A | 5/2000 | Ishihara | |
| 6,090,925 A | 7/2000 | Woiszwillo et al. | |
| 6,506,559 B1 * | 1/2003 | Fire et al. | 435/6 |
| 6,610,841 B1 * | 8/2003 | Warren | 536/25.3 |

FOREIGN PATENT DOCUMENTS

| | | |
|---|---|---|
| GB | A-1 440 626 | 6/1976 |
| WO | WO 91/14696 | 10/1991 |
| WO | WO 9630536 A1 * | 10/1996 |
| WO | WO 98/00172 | 1/1998 |
| WO | WO 99 30561 A | 6/1999 |
| WO | WO 00 50050 A | 8/2000 |
| WO | WO 00 78285 A | 12/2000 |

OTHER PUBLICATIONS

Dabrowiak, J.C., "MiniReview: Sequence Specificity of Drug-DNA Interactions", *Life Sciences*, 32:2915-2931 (1983).
Vedaldi, D., et al., "Sequence Specificity in DNA for the Interaction with Adriamycin or Daunomycin", *Il Farmaco—Ed. Sc.*, 9:571-581 (1982).
Chollet, A., "Selective Attachment of Oligonucleotides to Interleukin-1β and Targeted Delivery to Cells", *Nucleosides & Nucleotides*, 9(7):957-966 (1990).
Searle, M.S., "NMR Studies of Drug-DNA Interactions", *Progress in NMR Spectroscopy*, 25:403-480 (1993).
Rajur, S.B., et al., "Covalent Protein-Oligonucleotide Conjugates for Efficient Delivery of Antisense Molecules", *Bioconjugate Chem.*, 8:935-940 (1997).
McConnaughie, A.W. and Jenkins, T.C., "Novel Acridine-Triazenes as Prototype Combilexins: Synthesis, DNA Binding, and Biological Activity", J. Med. Chem., 38:3488-3501 (1995).
Morham, S.G. and Shuman, S., "Covalent and Noncovalent DNA Binding by Mutants of Vaccinia DNA Topoisomerase I*", *J. of Biol. Chem.*, 267(22):15984-15992 (1992).
Hill, G.C., et al., "Computer Simulation of the Binding of Naphthyridinomycin and Cyanocycline A to DNA", *J. Med. Chem.*, 34:2079-2088 (1991).
Hope, M.J., et al., "Cationic lipids, phosphatidylethanolamine and the intracellular delivery of polymeric, nucleic acid-based drugs (Review)", *Molecular Membrane Biology*, 15:1-14 (1998).
Garbesi, A., et al., "Synthesis and binding properties of conjugates between oligodeoxynucleotides and daunorubicin derivatives", *Nucleic Acids Research*, 25(11):2121-2128 (1997).
Jolles, B., et al., "Comparison of DNA sequence selectivity of anthracycline antibiotics and their 3'—hydroxylated analogs", *Chemico-Biological Interactions*, 100:165-176 (1996).
Gao, Q., et al., "Drug-induced Dna repair: X-ray structure of a DNA-ditercalinium complex", *Proc. Natl. Acad. Sci. USA*, 88:2422-2426 (1991).
Kumar, S., et al., "Solution structure of a highly stable DNA duplex conjugated to a minor groove binder", *Nucleic Acids Research*, 26(3):831-838 (1998).
Cummings, J., et al., "Determination of Covalent Binding to Intact DNA, RNA, and Oligonucleotides by Intercalating Anticancer Drugs Using High-Performance Liquid Chromatography. Studies with Doxorubicin and NADPH Cytochrome P-450 Reductase", *Analytical Biochemistry*, 194:146-155 (1991).
Cullinane, C., et al., "The DNA Sequence Specificity of Cyanomorpholinoadriamycin", *FEBS*, 293(1)(2):195-198 (1991).
Anderson, R.D., et al., "DNA Sequence Specificity of Doxorubicin-induced Mutational Damage in *uvrB- Escherichia coli*", *Cancer Research*, 51:3930-3937 (1991).
Trist, H. and Phillips, D.R., "In vitro transcription analysis of the role of flanking sequence on the DNA sequence specificity of Adriamycin", *Nucleic Acids Research*, 17(10):3673-3688 (1989).
Chaires, J.B., et al., "Site and Sequence Specificity of the Daunomycin-DNA Interaction", *Biochemistry*, 26:8227-8236 (1987).

(Continued)

*Primary Examiner* — Jon E Angell
(74) *Attorney, Agent, or Firm* — Choate, Hall & Stewart LLP; Brenda Herschbach Jarrell; Danielle Nihan

(57) ABSTRACT

Drug-carrier complexes, drug carriers, pharmaceutical formulations, methods of delivery drugs to an organism or tissue culture, methods of increasing the solubility of a substance, targeted carriers, drug delivery systems and implants are described. The compositions and methods of the invention include forming complexes having reversible associations between nucleotides and drugs. The compositions and methods of the invention can be employed to target drugs to cells, organisms or combinations of cells to treat and to study the underlying mechanisms of diseases, and to test drug candidates.

43 Claims, 4 Drawing Sheets

OTHER PUBLICATIONS

Pearlman, L.F. and Simpkins, H., "The Differential Effects Produced by Daunomycin and Adriamycin on RNA, Polynucleotides, Single Stranded, Supercoiled DNA, and Nucleosomes", *Biochemical and Biophysical Research Communications*, 131(2):1033-1040 (1985).

Wang, L., et al., "Inhibition of Topoisomerase I Function by Nitidine and Fagaronine", *Chem. Res. Toxicol.*, 6:813-818 (1993).

Capranico, G., et al., "Change of the Sequence Specificity of Daunorubicin-stimulated Topoisomerase II DNA Cleavage by Epimerization of the Amino Group of the Sugar Moiety", Cancer Research, 55:312-317 (1995).

Capranico, G., et al., "Conformational Drug Determinants of the Sequence Specificity of Drug-stimulated Topoisomerase II DNA Cleavage", *J. Mol. Biol.*, 235:1218-1230 (1994).

Capranico, G., et al., "Unique Sequence Specificity of Topoisomerase II DNA Cleavage Stimulation and DNA Binding Mode of Streptonigrin", *J. Biol. Chem.*, 269(40):25004-25009 (1994).

Cullinane, C., et al., Formation of adriamycin—DNA adducts in vitro, *Nucleic Acids Research*, 22(12):2296-2303 (1994).

Cullinane, C. and Phillips, D.R., "Sequence Specificity of (Cyanomorpholino) adriamycin Adducts in Human Cells", *Biochemistry*, 33:6207-6212 (1994).

Cornarotti, M., et al., "Drug Sensivity and Sequence Specificity of Human Recombinant DNA Topoisomerases II$\alpha$ (p170) and II$\beta$ (p180)", *The American Society for Pharmacology and Experimental Therapeutics*, 50:1463-1471 (1998).

Binaschi, M., et al., "Relationship between Lethal Effects and Topoisomerase II-Mediated Double-Stranded DNA Breaks Produced by Anthracyclines with Different Sequence Specificity", *The American Society for Pharmacology and Experimental Therapeutics*, 51:1053-1059 (1997).

Gao, Y., et al., "Substitutions at C2' of daunosamine in the anticancer drug daunorubicin alter its DNA-binding sequence specificity", *Am. J. Biochem.*, 240:331-335 (1996).

Sriram, M., et al., "Molecular Structure of Antitumor Drug Steffimycin and Modelling of its Binding to DNA", *J. Biomolecular Structure & Dynamics*, 9(2):251-269 (1991).

Pullman, B., "Sequence specificity in the binding of anti-tumor anthracyclines to DNA: a success of theory", *Anti-Cancer Drug Design*, 7:95-105 (1991).

van Houte, L.P.A., et al., "The Antitumor Drug Nogalamycin Forms Two Different Intercalation Complexes with d(GCGT)-d(ACGC)", *Biochemistry*, 32:1667-1674 (1993).

Capranico, G., et al., "Similar Sequence Specificity of Mitoxantrone and VM-26 Stimulation of in Vitro DNA Cleavage by Mammalian DNA Topoisomerase II", *Biochemistry*, 32:3038-3046 (1993).

D'Incalci, M., "DNA-topoisomerase inhibitors", *Current Opinion in Oncology*, 5:1023-1028 (1993).

Phillips, D.R., et al., "DNA sequence-specific adducts of adriamycin and mitomycin C", *FEBS*, 246(1)(2):233-240 (1989).

Borgnetto, M.E., et al., "Drug-specific Sites of Topoisomerase II DNA Cleavage in *Drosophila* Chromatin: Heterogeneous Localization and Reversibility", *Cancer Research*, 56:1855-1862 (1996).

Mee, S.L., et al., "S16020-2, a New Highly Cytotoxic Antitumor Olivacine Derivative: DNA Interaction and DNA Topoisomerase II Inhibition", *Molecular Pharmacology*, 53:213-220 (1998).

Patel, D.J., et al., "Hydrogen bonding, overlap geometry, and sequence specificity in anthracycline antitumor antibiotic: DNA complexes in solution", *Proc. Natl. Acad. Sci. USA*, 78(6):3333-3337 (1981).

Phillips, D.R., "Kinetics and Sequence Specificity of Drug-DNA Interactions: An in Vitro Transcription Assay", *Biochemistry*, 25:7355-7362 (1986).

Skorobogaty, A., et al., "Elucidation of the DNA Sequence Preferences of Daunomycin", *Drug Design and Delivery*, 3:125-151 (1988).

Hook, R.J., et al., "Synthesis of polyamine-linked bis-daunomycin hydrazones and their interaction with DNA", *Anti-Cancer Drug Design*, 4:173-189 (1989).

Taatjes, D.J., et al., "Epidoxoform: A Hydrolytically More Stable Anthracycline-Formaldehyde Conjugate Toxic to Resistant Tumor Cells", *J. Med. Chem.*, 41:1306-1314 (1998).

Rizzo, V., et al., "Association of Anthracyclines and Synthetic Hexanucleotides. Structural Factors Influencing Sequence Specificity", *J. Molec. Recognition*, 2(3):132-141 (1989).

Krugh, T.R., "Drug-DNA interactions", *Current Opinion in Structural Biology*, 4:351-364 (1994).

Hashida, M. et al., "Targeted delivery of plasmid DNA complexed with galactosylated poly(L-lysine)," *Journal of Controlled Release* 53:301-310 (1998).

Veronese F.M. and M. Morpurgo, "Bioconjugation in pharmaceutical chemistry," *Il Farmaco* 54:497-516 (1999).

Zangemeister-Wittke, U. et al., "Synergic cytotoxicity of bcl-2 antisense oligodeoxynucleotides and etoposide, doxorubicin and cisplatin on small-cell lung cancer cell lines," *British Journal of Cancer* 78(8):1035-1042 (1998).

Oxenius, A. et al., "CpG-Containing Oligonucleotides Are Efficient Adjuvants for Induction of Protective Antiviral Immune Responses with T-Cell Peptide Vaccines," *J. Virol.* 73(5):4120-4126 (1999).

Bonora, G. M. et al., "Synthesis and Characterization of High-Molecular Mass Polyethylene Glycol-Conjugated Oligonucleotides," *Bioconjugate Chem.* 8(6):793-797 (1997).

Database PUBMED, Accession Number: 9404651, Bonora, G. M. et al., "Synthesis and Characterization of High-Molecular Mass Polyethylene Glycol-Conjugated Oligonucleotides," [online], [retrieved from MEDLINE on Jan. 13, 2003], (1997).

Katayose, S. et al., "Water-Soluble Polyion Complex Associates of DNA and (Poly(ethylene glycol)-Poly(L-lysine) Block Copolymer," *Bioconjugate Chem.* 8(5):702-707 (1997).

Database PUBMED, Accession No: 9327134, Katayose, S. et al., "Water-Soluble Polyion Complex Associates of DNA and Poly(ethylene glycol)-Poly(L-lysine) Block Copolymer," [online], [retrieved from MEDLINE on Jan. 13, 2003], (1997).

Jäschke, A. et al., "Synthesis and Properties of Oligodeoxyribonucleotide-Polyethylene Glycol Conjugates," *Nucleic Acids Res*. 22(22):4810-4817 (1994).

Database PUBMED, Accession No: 7984434. Jäschke, A. et al., "Synthesis and Properties of Oligodeoxyribonucleotide-Polyethylene Glycol Conjugates,"[online], [retrieved from MEDLINE on Jan. 13, 2003], (1994).

Kawaguchi, T. et al., "Stability, Specific Binding Activity, and Plasma Concentration in Mice of an Oligodeoxynucleotide Modified at 5'-Terminal with Poly(ethylene glycol)," *Biol. Pharm. Bull*. 18(3):474476 (1995).

Database PUBMED, Accession No: 7550108, Kawaguchi, T. et al., "Stability, Specific Binding Activity, and Plasma Concentration in Mice of an Oligodeoxynucleotide Modified at 5'-Terminal with Poly-(ethylene glycol)," [online], [retrieved from MEDLINE on Jan. 13, 2003], (1995).

Wang, J. et al., Use of a Polytheylene Glycol-Peptide Conjugate in a Competition Gel Shift Assay for Screening Potential Antagonists of HIV-1 Tat Protein Binding to TAR RNA, *Anal. Biochem*. 232:238242 (1995).

Database PUBMED, Accession No: 8747481. Wang, J. et al., "Use of a Polytheylene Glycol-Peptide Conjugate in a Competition Gel Shift Assay for Screening Potential Antagonists of HIV-1 Tat Protein Binding to TAR RNA," [online], [retrieved from MEDLINE on Jan. 13, 2003], (1995).

Matysiak, S., et al., *Nucleosides & Nucleotides*, 16 (5&6), 855-861, (1997).

Ziegler, A., et al., "Induction of Apoptosis in Small-Cell Lung Cancer Cells by an Antisense Oligodeoxynucleotide Targeting the Bcl-2 Coding Sequence," *Journal of the National Cancer Institute* 89(14):1027-1036 (1997).

Yang, X.-L. and Wang, A. H.-J., "Structural Studies of Atom-Specific Anticancer Drugs Acting on DNA," *Pharmacology & Therapeutics* 83:181-215 (1999).

Lipscomb, L.A., et al., "Water Ring Structure at DNA Interfaces: Hydration and Dynamics of DNA-Anthracycline Complexes," *Biochemistry* 33:3649-3659 (1994).

Herschlag, D., et al., "An RNA Chaperone Activity of Non-Specific RNA Binding Proteins in Hammerhead Ribozyme Catalysis," *The EMBO Journal* 13(12):2913-2924 (1994).

Huff, A.C. and Kreuzer, K.N., "Evidence for a Common Mechanism of Action for Antitumor and Antibacterial Agents That Inhibit Type II DNA Topoisomerases," *The Journal of Biological Chemistry* 265(33):20496-20505 (1990).

US 5,484,894, 01/1996, Woiszwillo (withdrawn)
US 5,849,884, 12/1998, Woiszwillo et al. (withdrawn)

\* cited by examiner

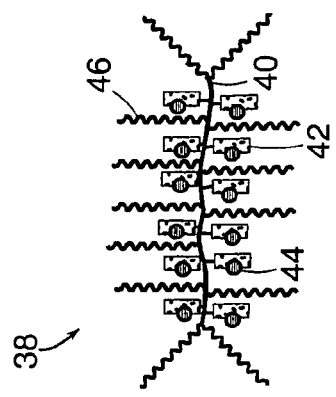
FIG. 3A
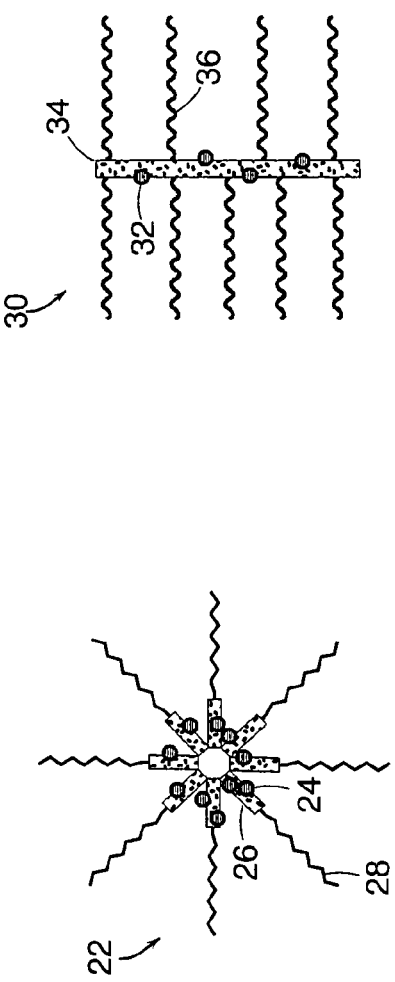
FIG. 3B
FIG. 3C
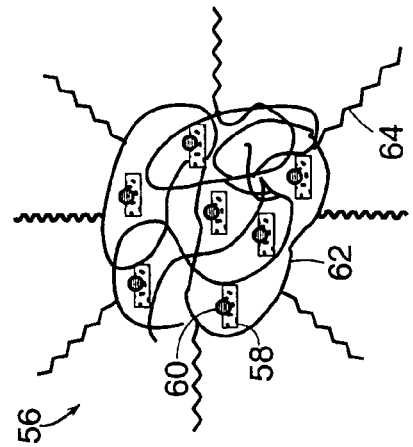
FIG. 3D
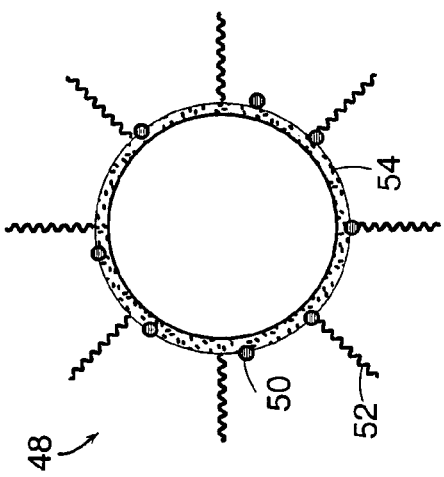
FIG. 3E

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 1
aaatctccca gcgtgcgcca taa                                            23

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<223> OTHER INFORMATION: t = amino modified T

<400> SEQUENCE: 2
ttatggcgca cgctgggaga ttt                                            23

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
cgtcgacgtc gaatatacgc                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
gcgtatattc gacgtcgacg                                                20

<210> SEQ ID NO 5
<211> LENGTH: 21
```

```
<212> TYPE: DNA
<213> ORGANISM: Artificial Sequence
<220> FEATURE:
<223> OTHER INFORMATION: Synthetic Oligonucleotide

<400> SEQUENCE: 5
tttctctctc tctctctctc t                                           21

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
agagagagag agagagagaa aa                                          22

<210> SEQ ID NO 7
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 7
atggcgcacg ctgggaga                                               18

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<223> OTHER INFORMATION: c indicates an RNA base

<400> SEQUENCE: 8
tctcccagcg tgcgccatc                                              19

<210> SEQ ID NO 9
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<223> OTHER INFORMATION: c indicates an RNA base

<400> SEQUENCE: 9
atggcgcacg ctgggagac                                              19

<210> SEQ ID NO 10
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 10
tttctctctc tctctctctc t                                           21

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 11
cgtcgacgtc gaatatacgc                                                  20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
gcgtatattc gacgtcgacg                                                  20

<210> SEQ ID NO 13
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 13
acttgccatt                                                             10
```

DRUG-CARRIER COMPLEXES AND METHODS OF USE THEREOF

RELATED APPLICATIONS

This application is a continuation of U.S. Utility application Ser. No. 09/634,320, filed Aug. 9, 2000, now U.S. Pat. No. 6,822,086 and claims the benefit of U.S. Provisional Application Ser. No. 60/147,919, filed Aug. 9, 1999, the entire teachings of which are incorporated herein by reference.

BACKGROUND OF THE INVENTION

Many drugs mediate their effects on cells by interacting with (e.g., binding) nucleic acid sequences in cells. Interactions of drugs with nucleic acid sequences in cells (e.g., DNA of a cancerous cell) can stop cellular proliferation or cause cell death, thereby halting the progression of a disease state. However, many drugs employed to treat diseases are either insufficiently soluble in aqueous solutions or have adverse side effects, such as the death of healthy cells, because of the lack of suitable substances to deliver drugs to a cell or organism (e.g., mammal) requiring treatment.

There have been many attempts to overcome problems generally associated with drug delivery. For example, macromolecular drug-carriers, which most commonly are water-soluble macromolecules with chemically associated drug molecules, often are employed to prolong drug circulation, limit renal clearance, increase drug accumulation in target tissues or cells, and to decrease drug concentration in normal tissues. Several model and prototype carriers of this type have been developed. Potentially, these carriers can be as small as 5-10 nanometers (nm), but depending on the drug structure and content, they often form larger (20-50 nm) associates. Carriers of this type are intended to act, essentially, as prodrugs, the drug substance as a result of degradation of the drug-carrier bond. Some carriers of this type have been targeted to cancer cell markers. Examples of this class of drug-carriers are: dextran-mitomycin conjugates; HPMA-doxorubicin conjugates with enzyme-degradable peptide bonds between the drug molecule and the backbone polymer; doxorubicin-Fab conjugates with pH-sensitive bonds between doxorubicin molecules and the Fab. Although potentially useful, carriers of this type have at least two potential drawbacks.

First, drug release via degradation of the drug-carrier bond generally is irreversible. Thus, drug released from the carrier will circulate in the body independently of the carrier, which may reduce the efficacy of drug delivery. Drug release via enzyme-dependent or pH-dependent hydrolysis has been reported to improve the ratio of drug activity in the target relative to normal tissues. However, expression of enzymes, such as proteases, in tumors and other pathologies is highly variable, which makes predictability of release rate of the drug difficult. Enzyme-independent biodegradation, on the other hand, can occur in both pathological and normal tissues.

A second problem relates to exposure to the environment of drug molecules attached to the macromolecular backbone. This can result in cross-interaction of drug moieties with formation of intramolecular and intermolecular micelles, interactions with tissue components altering drug-carrier adduct biodistribution, and other undesirable effects. These effects are expected to be partially suppressed via "steric protection," or modification of the carrier backbone with hydrophilic polymer chains such as, for example, polyethyleneglycol, dextran, or PHF (polyhydroxymethylethylene hydroxymethylformal). However, in sterically protected carriers, enzyme access to enzyme-sensitive drug-carrier bonds also may be suppressed.

Another attempt to overcome problems associated with drug delivery includes combination of drugs with microparticles and emulsions. Microparticles and emulsions were developed as an alternative where the drug molecules are not bound chemically, but rather are adsorbed on, or dissolved in, the material of the carrier. However, particles and emulsions do not circulate in vivo long enough and accumulate in the reticuloendothelial system (RES) and other organs, unless the particle (droplet) surface is modified with a hydrophilic polymer, such as PEG. The overall size of sterically protected particles (droplets) is usually above about 25 nm. Major problems in the development of such carriers include the fact that (1) the emulsions generally are relatively unstable and change (e.g. coalesce) in storage; (2) high-scale production of both submicron particles and emulsions typically is difficult; and (3) drug molecules released from the particles or droplets will circulate independently of the carrier. Emulsions and most particles are not suitable for transport of hydrophilic drugs.

A specific development in drug delivery was employment of micelles, which were developed as "self-assembling" drug carriers similar to particles and emulsions. They are made of surfactants, which are usually block copolymers, where one of the blocks is hydrophilic, and the other hydrophobic. The total hydrodynamic size of the micelles usually is 10-30 nm. The hydrophobic drug molecules either are incorporated into the hydrophobic core or, alternatively, chemically conjugated with one of the blocks and form the hydrophobic core. Some of the problems in the development of such carriers are similar to those described above. In addition, none of these carriers can reabsorb specifically the released drug; drug release rate is difficult to control, and amphiphylic components can produce toxic effects. These carriers are not suitable for transport of hydrophilic drugs.

Still another attempt includes encapsulation of drugs in the aqueous compartments of liposomes, which are vesicles, typically having a diameter in a range of between about 50 and about 1000 nm. However the efficacy of drug encapsulation and the potential to control drug delivery by incorporation into liposomes can be problematic. For example, drug release from liposomes generally is irreversible. Further, liposome penetration into tumors or tumor zones that have relatively low vascular permeability often is poor. Also, there are many problems associated with high-volume production and storage of liposomal preparation that present significant technical challenges.

Other systems employed to bind drugs for delivery to a cell or an organism have similar drawbacks. Thus, there is a need for a method to deliver drugs that minimize or overcome the above-referenced problems.

SUMMARY OF THE INVENTION

The present invention relates to the field of drug delivery, in particular to methods of forming drug-carrier complexes and the use of drug-carrier complexes as pharmaceutical compositions to deliver and target drugs in an organism, tissue culture or cells.

In one embodiment, the method includes forming a drug-carrier complex by combining at least one nucleotide strand with a drug, whereby the drug and the nucleotide strand reversibly associate with each other to form a drug-carrier complex.

In another embodiment, the method includes forming a drug-carrier complex by combining a drug with at least two nucleotide strands that hybridize with each other, whereby the drug associates with the nucleotide strands to form a water soluble drug-carrier complex.

In still another embodiment, the method includes forming a drug-carrier composition by combining a drug component and a nucleotide component. The combined drug and nucleotide components are lyophilized to form the drug-carrier composition.

In yet another embodiment, the method includes forming a drug-carrier composition by lyophilizing a drug component, lyophilizing a nucleotide component and combining the lyophilized drug component and the lyophilized nucleotide component to form the drug-carrier composition.

Another embodiment of the invention is a drug carrier, comprising a double-stranded nucleotide and a polymer component covalently bonded to at least one strand of the double-stranded nucleotide. The polymer component has an aqueous solubility of at least one mg/liter at 25° C.

An additional embodiment of the invention is a drug carrier, comprising a double-stranded nucleotide and an oligomer component covalently bonded to at least one strand of the double-stranded nucleotide.

In an additional embodiment, the invention is a drug-carrier complex, comprising a single-stranded nucleotide, a drug reversibly associated with the single-stranded nucleotide and a polymer associated with the drug or the single-stranded nucleotide.

In yet another embodiment, the invention is a drug-carrier complex, comprising a single-stranded nucleotide, an oligomer associated with the single-stranded nucleotide and a drug reversibly associated with the oligomer or the single-stranded nucleotide.

In still another embodiment, the invention is a drug carrier, comprising a single-stranded nucleotide and at least two polymers associated with the single-stranded nucleotide.

In another embodiment, the invention is a drug carrier, comprising an oligomer, a single-stranded nucleotide entrapped by the oligomer and a drug reversibly associated with the single-stranded nucleotide.

In still another embodiment, the invention is a drug-carrier composition, comprising a nucleotide carrier component and a drug component. The drug-carrier composition has a moisture content less than about 5% by weight.

In yet another embodiment, the invention includes a drug-carrier composition consisting essentially of a drug component and a nucleotide component.

In an additional embodiment, the invention is a pharmaceutical formulation, comprising a nucleotide carrier component and a drug in reversible association with the nucleotide carrier component.

In still another embodiment, a method of the invention includes delivering a drug to an organism by administering a drug-carrier complex to the organism. The drug-carrier complex includes a nucleotide carrier and a drug in reversible association with each other.

In another embodiment, a method of the invention includes delivering a drug to a tissue culture by administering a drug-carrier complex to the tissue culture. The drug-carrier complex includes a nucleotide carrier and a drug in reversible association with each other.

In yet another embodiment, the method includes delivering a drug to an organism by administering a drug and a nucleotide carrier, which reversibly associates with the drug to form a drug-carrier complex, to the organism.

In still another embodiment, the method includes delivering a drug to an organism by forming a drug carrier complex that includes a drug and a nucleotide strand in reversible association with the drug and administering the drug-carrier complex to the organism.

Another embodiment includes a method of delivering a drug to an organism by administering to the organism a drug-carrier complex. The drug-carrier complex includes a drug component and a carrier component in reversible association with each other. The drug can dissociate from the drug-carrier complex and reassociate with the carrier component. The degree of association can depend, for example, on the concentrations of the drug and the carrier.

In still another embodiment, the method includes increasing aqueous solubility of a substance by reversibly associating the substance with a nucleotide carrier to form a water-soluble complex.

In yet another embodiment, the invention is a targeted carrier, comprising a nucleotide, a polymer component associated with the nucleotide, and a ligand associated with the nucleotide or the polymer component and associable with a cell or tissue marker. The cell or tissue marker is selected from the group consisting of proteins, peptides, carbohydrates, lipids and nucleotides.

In still another embodiment, the invention relates to a targeted carrier, comprising a nucleotide, a polymer component associated with the nucleotide and a ligand. The ligand is associated with the nucleotide or the polymer component and is associable with a cell or tissue marker. The cell or tissue marker is selected from the group consisting of proteins, peptides, carbohydrates, lipids and nucleotides.

In an additional embodiment, the invention relates to a targeted drug-carrier complex, comprising a nucleotide, a drug reversibly associated with the nucleotide and a targeting component. The targeting component is associated with the nucleotide or the drug. The targeting component includes a ligand associable with a cell or tissue marker. The cell or tissue marker is selected from the group consisting of proteins, peptides, carbohydrates, lipids and nucleotides.

In yet another embodiment, the invention relates to a targeted drug-carrier complex, comprising a nucleotide, a drug reversibly associated with the nucleotide, a polymer component associated with the nucleotide or the drug and a targeting component. The targeting component is associated with the nucleotide, the drug or the polymer. The targeting component includes a ligand associable with a cell or tissue marker. The cell or tissue marker is selected from the group consisting of proteins, peptides, carbohydrates, lipids and nucleotides.

In an additional embodiment, the invention relates to a drug delivery system, comprising a matrix, a nucleotide associated with or entrapped within the matrix and a drug in reversible association with the nucleotide.

Another embodiment includes an implant, comprising an implant matrix, a nucleotide associated with or entrapped within the matrix and a drug in reversible association with the nucleotide.

The invention described herein provides drug-carrier complexes, drug-carrier compositions, drug carriers, pharmaceutical formulations, methods of delivery drugs to organisms and tissue cultures, targeted carriers and implants to deliver drugs to an organism, a tissue culture or a combination of cells. The nucleotide-based drug delivery systems of the present invention have many advantages. For example, they can transport drugs in chemically unmodified form, and can reabsorb the released drug. By employing a reversible drug association, the drug delivery systems of this invention are able to reincorporate the released drug. Thus, drug behavior in the tissues may remain dependent on the drug release system for as long as the latter remains functional, which offers the possibility of new opportunities in regulation of pharmacokinetics and pharmacodynamics. In a clinical setting, this is expected to result in better biological functionality and broader safety margins of pharmaceutical formulations and devices.

Other advantages include, for example, a relatively small size of the drug-carrier complex, such as, for example, about 3 or about 5 nm. The drug-carrier complex can be, for example, 5 to 10 times smaller than polymer- and micelle-based carriers, and at least 10 to 20 times smaller than liposomes. Therefore, drug penetration into certain tissues, such as cancerous tissues, may be significantly more efficient, especially where endothelial and interstitial barriers are high. Also, stability and release rates of drug-carrier complexes of the invention can be controlled within a broad range, thereby providing the opportunity to design products in accordance with specific clinical objectives. Further, release of drugs by the drug-carrier complexes of the invention does not require interactions with enzymes, cells or other factors, thereby making the drug-carrier complexes more independent of the organism and tissue state. Alternatively, however, complexes of the invention can be designed to exploit specific conditions of an organism or tissue state, such as pH or enzyme content. In addition, the components of the drug-carrier complexes of the invention can be made of close analogs of natural components of biological systems which are known to be completely biodegradable and non-toxic.

Other specific advantages of the invention include the possibility of steric protection against carrier clearance and drug inactivation. Also, the drug-carrier complexes of the invention generally have no problems relevant to intramolecular or intermolecular association of drug molecules. Further, methods of forming and processing the drug-carrier complexes of the invention are readily scalable. Also, drug-carrier complexes are lyophilizable, and all components of the complexes can be stable in the presence of air. Further, no toxic surfactants are employed, the size of the complexes generally is stable and does not depend on conditions and concentration. Drug release rate within an organism generally does not depend on highly variable adsorption forces. Ultrafiltration typically does not affect size and structure of the drug-carrier complexes.

BRIEF DESCRIPTION OF THE FIGURES

FIGS. 3A, 3B, 3C, 3D and 3E depict additional embodiments of drug delivery complexes of the invention, portraying various arrangements of drug, polynucleotide or oligonucleotide, and polymer components of the complexes.

DETAILED DESCRIPTION OF THE INVENTION

Figure 1A:
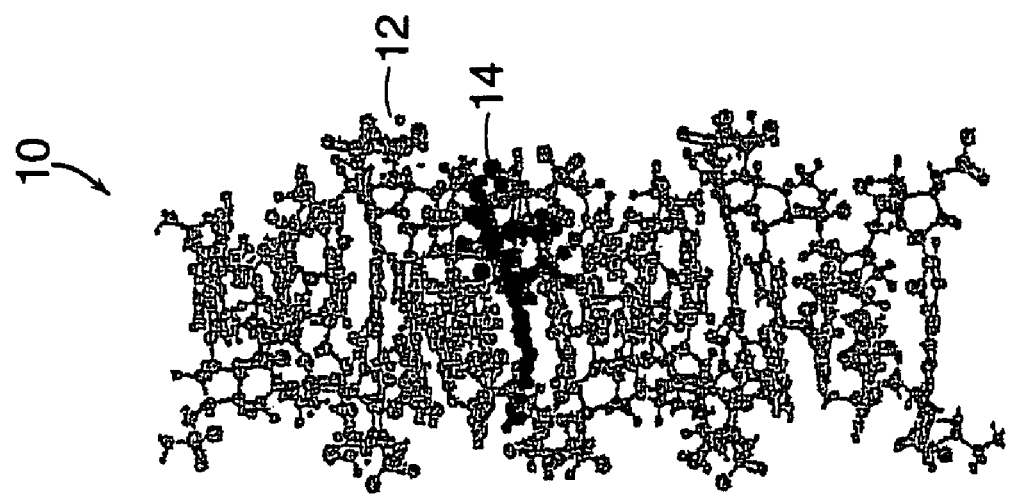
FIG. 1A depicts the intercalation of doxorubicin (darkly shaded) with B-helical DNA in a space-filled model of one embodiment of the drug-carrier complex of the invention.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention relates to the discovery that useful drug-carrier complexes can be formed by combining a nucleotide (e.g., nucleotide strands) with a drug so that the drug and nucleotide are in reversible association with either other. The drug-carrier complex can be used to deliver drugs to, for example, an organism, a tissue culture, or individual cells. The invention further relates to the discovery that the drug-carrier complexes of the invention can be used in pharmaceutical formulations to increase the solubility of drugs, as targeted carriers, as drug delivery systems and as implants.

In one embodiment, a drug-carrier complex is formed by combining at least one nucleotide strand with a drug. The drug is in reversible association with the nucleotide component to form the drug-carrier complex. Thus, a "drug-carrier complex," as used herein, (also referred to as a "nucleotide-carrier complex") refers to at least one nucleotide strand and a drug that are in reversible association with each other.

The terms "associate," "association," or "associable," as used herein, can be reversible, irreversible or both. The association can be a physical association, a chemical association or both. For example, an association can be a covalent bond, a hydrophobic interaction, etc.

A "reversible association," as defined herein, is an association wherein the components can return to an original, pre-association, state. For example, a reversible association of the components of a drug-carrier complex of the invention can disassociate and thereby return to original and distinct drug and nucleotide components.

In one embodiment, the amount of association of components of a reversible association depends, at least in part, on the concentration of the drug and the carrier. In another embodiment, the components are dissociable under physiological conditions. In a specific embodiment, the reversible associations are associations selected from the group consisting of electrostatic bonding, hydrogen bonding, van der Waals forces, ionic interaction or donor/acceptor bonding. The reversible association can be mediated by one or more associations between the drug and the nucleotide strand. For example, the reversible association can include a combination of hydrogen bonding and ionic bonding between the drug and the nucleotide strand. Additionally, or alternatively, the reversible association can be in combination with, for example, covalent or other noncovalent interactions between components, such as between a drug and a nucleotide.

In another specific embodiment of a drug-carrier complex of the invention, a substance comprising a metal containing substance, (e.g., platinum, cis-platinum, carboplatin, platinum, gold, silver) is reversibly associated with nucleotide carriers. The association is considered to be non-covalent and can reversibly release a metal-containing biologically active drug component that can differ from the substance originally employed to form the drug-carrier complex.

As employed herein, the terms "nucleotide," "nucleotide strand," or "nucleotide carrier" describe a molecule consisting essentially of either naturally occurring nucleosides, (e.g., containing base components guanine (G), thymine (T), uracil (U), cytosine (C), adenine (A)), or their derivatives, or structural analogs. A nucleotide strand comprises two or more nucleotides, e.g., an oligonucleotide, a polynucleotide, or a chemical derivative or an analog thereof. The term "oligonucleotide" generally describes a molecule with well-defined structure and length (e.g., 5'-ACTTGCCATT, SEQ ID NO: 13). The term "polynucleotide" generally refers to molecules assembled from a large number of nucleosides, where either the sequence or the length of the polynucleotide varies (e.g., preparations of DNA or RNA obtained from cell lysates, random polymers of the structure $A_n T_m G_k C_j$).

In naturally occurring oligonucleotides and polynucleotides, the bases usually are connected via phosphodiester linkages. Several chemical analogs are known, where bases are connected via non-phosphodiester linkages.

Nucleotide strands may exist in linear and circular forms and are known to form a variety of structures, e.g., helical double strands (helixes), triple strands (often referred to as triplexes), loops, folds, crosses or supercoils.

This invention utilizes all types of nucleotide strands, structures and combinations formed thereof, including, for example, linear deoxyribonucleotides, linear ribonucleotides, linear oligonucleotides comprising both ribonucleotides and deoxyribonucleotides, circular DNA (e.g., plasmids), folded ribonucleotides (e.g., ribozymes, t-RNA), viral RNA, viral DNA; DNA and RNA from cell lysates; synthetic polydeoxyribonucleotides and polyribonucleotides, chemically crosslinked double-stranded oligonucleotides, partially or completely methylated or otherwise chemically altered forms of any of the above.

The preferred nucleotides of this invention are nucleotides with well-defined structures, such as synthetic oligonucleotides, plasmids, RNA transcripts, viral DNA, and viral RNA (e.g., viral nucleotides in the viral envelope, intact virions, viruses). Other preferred nucleotides are synthetic oligonucleotides chemically modified such that to modulate their biodegradation rate (e.g., oligonucleotides comprising phosphorothioate linkages) or to enable conjugation with other molecules (for example, synthetic oligonucleotides with a carboxyl or an amino group incorporated at 3'-end, 5'-end, or at one or more of the bases).

The DNA of a nucleotide strand can be B DNA (Drew, H. R., et al., *Proc. Natl. Acad. Sci. U.S.A.*, 78:2179-2183 (1981); Edwards, K. J., et al., *J. Mol. Biol.*, 226:1161-1173 (1992), the teachings of both of which are hereby incorporated by reference in their entirety); Z DNA (Gessner, R. V., et al., *J. Biol. Chem.*, 264:7921-7935 (1989), the teachings of which are hereby incorporated by reference in its entirety); triplex DNA (Van Meervelt, L., et al., *Nature*, 374, 742-744 (1995), the teachings of which are hereby incorporated by reference in its entirety); intramolecular triplex DNA (Koshlap, K. M., et al., *Biochemistry* 36:2659 (1997); intercalated 4-stranded DNA (Kang, C., et al., *Proc. Natl. Acad. Sci. U.S.A.* 91:11636-11640 (1994); Kang, C., et al., *Proc. Natl. Acad. Sci. U.S.A.*, 92:3874-3878 (1995), the teachings of both of which are hereby incorporated by reference in their entirety); quadruplex DNA (Kang, C., et al., *Nature* 356:26-131 (1992), the teachings of which are hereby incorporated by reference in its entirety); or bulge loop DNA (Joshua-Tor, L., et al., *J. Mol. Biol.*, 225: 397-431 (1992), the teachings of which are hereby incorporated by reference in its entirety).

The nucleotides or nucleotide strands can be naturally occurring (e.g., isolated from cells of an organism, from tissue culture cells, a virus) or can be synthetically generated by, for example, a nucleotide synthesis apparatus. The residues can be modified further after synthesizing the nucleotide strand. For example, the 5'-amino group of a nucleotide strand can be modified with N-hydroxy succinimide ester of carboxy-polyethyleneglycol. Nucleosides typically occurring in nature can be used in conjunction with nucleosides not typically occurring in nature to synthesize the nucleotides and nucleotide strands employed by the invention. Methods to isolate nucleotides or nucleotide strands from cells, tissues or organisms, as well as methods to synthesize nucleotides or nucleotide strands in commercially available DNA/RNA synthesis machines, are well known in the art. Exemplary techniques are described, for example, in "Current Protocols in Molecular Biology" (Ausubel et al., John Wiley & Sons (1999), the teachings of which are hereby incorporated by reference in their entirety).

The term "nucleotide component" refers to the drug-binding (drug carrying) component of the of the drug-carrier complexes of this invention. The drug-binding component comprises at least one nucleotide strand. The nucleotide component may include, or be further associated with, other components (e.g. polymers, oligomers, ligands) to form drug carrier, a drug delivery system, or a drug-laden implant. In one embodiment, the nucleotide strand is an oligonucleotide strand.

The drug of the drug-carrier complex can be any substance that binds reversibly (also referred to herein as "reversibly associates" or "is in reversible association") with a nucleotide or nucleotide strand, or any structures formed by said strands, of the invention. The drug can reversibly associate with a single nucleotide of one or more nucleotide strands, for example via a donor-acceptor bond. The drug can also reversibly associate with more than one nucleotide of one or more nucleotide strands. The drug can reversibly associate with one nucleotide strand of a drug-carrier complex consisting of two nucleotide strands. Likewise, the drug can reversibly associate with two nucleotide strands of a drug-carrier complex consisting of two nucleotide strands. Similarly, the drug can reversibly associate with a single nucleotide strand of a drug-carrier complex consisting of three nucleotide strands.

The term "drug" is used herein interchangeably with the phrase "drug component." In one embodiment, the drug of the pharmaceutical formulation is a therapeutic drug. The term "therapeutic," when referring to a drug used in the invention, refers to a drug used to treat, remediate or cure a disorder or a disease (e.g., hereditary diseases, viral diseases such as AIDS, cancer). In another embodiment, the drug of the pharmaceutical formulation is a diagnostic drug (e.g., a radioactive diagnostic drug, a flourescent diagnostic drug, a paramagnetic diagnostic drug, superparamagnetic diagnostic drug, an x-ray dense diagnostic drug or an electron dense diagnostic drug). The term "diagnostic," when referring to a drug employed in the invention, refers to a drug employed to determine the nature or extent of a disease, or employed to confirm the presence of a disorder or a disease.

In other embodiments, the drug can be, for example, an anticancer drug, antiviral drug, antibacterial drug, or antiprotozoal drug. The drug can also be, for example, anthracycline, actinomycin, anthracenedione, bleomycin, mithramycin, chromomycin, olivomycin, protein, peptide, carbohydrate, polyamine, polycation, actinomycin D, daunorubicin, doxorubicin, idarubicin, bis-anthracycline, mitoxantrone, bleomycin A2, distamycin, netropsin, cisplatin, carboplatin, a silver ion and particle, or a gold ion and particle.

In one embodiment, the drug is an oligonucleotide drug. The phrase "oligonucleotide drug," as used herein, refers to a molecule containing at least two nucleotides which binds reversibly to the nucleotide strand of the drug-carrier complex. The oligonucleotide drug can be, for example, an antisense oligonucleotide or a ribozyme. Examples of other suitable drugs include a component such as a metal containing substance (e.g., platinum, cis-platinum, carboplatin, platinum, gold, silver), or a drug that binds the minor or major groove of DNA or RNA helix. In yet another embodiment, the drug includes at least one amino group. For example, the drug doxorubicin includes an amino group.

Figure 1B:
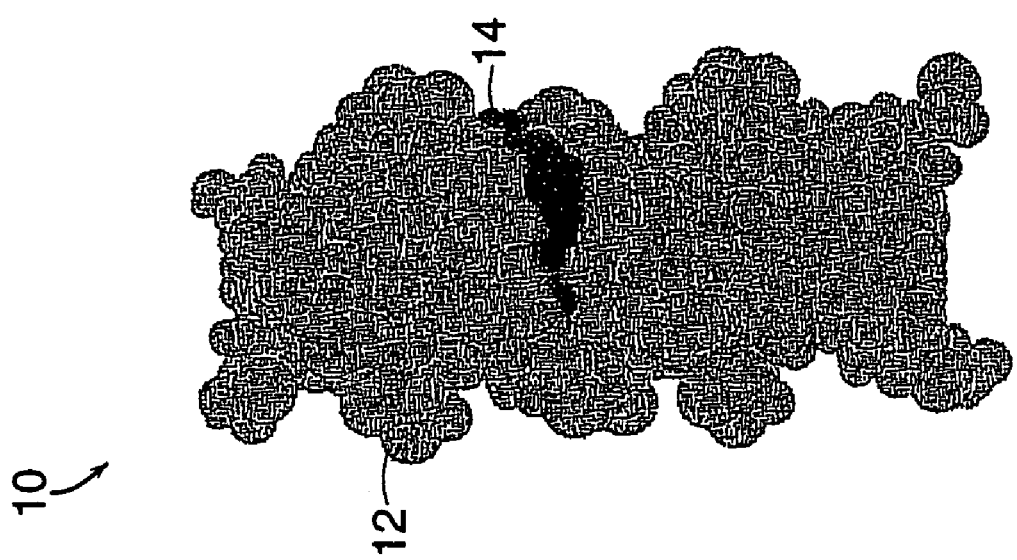
FIG. 1B depicts the intercalation of doxorubicin (darkly shaded) with B-helical DNA in a ball and stick model of another embodiment of the drug-carrier complex of the invention.

In another embodiment, and as shown in FIGS. 1A and 1B, drug complex 10 includes nucleotide 12 and drug 14 that intercalates with nucleotide 12.

Figure 2:
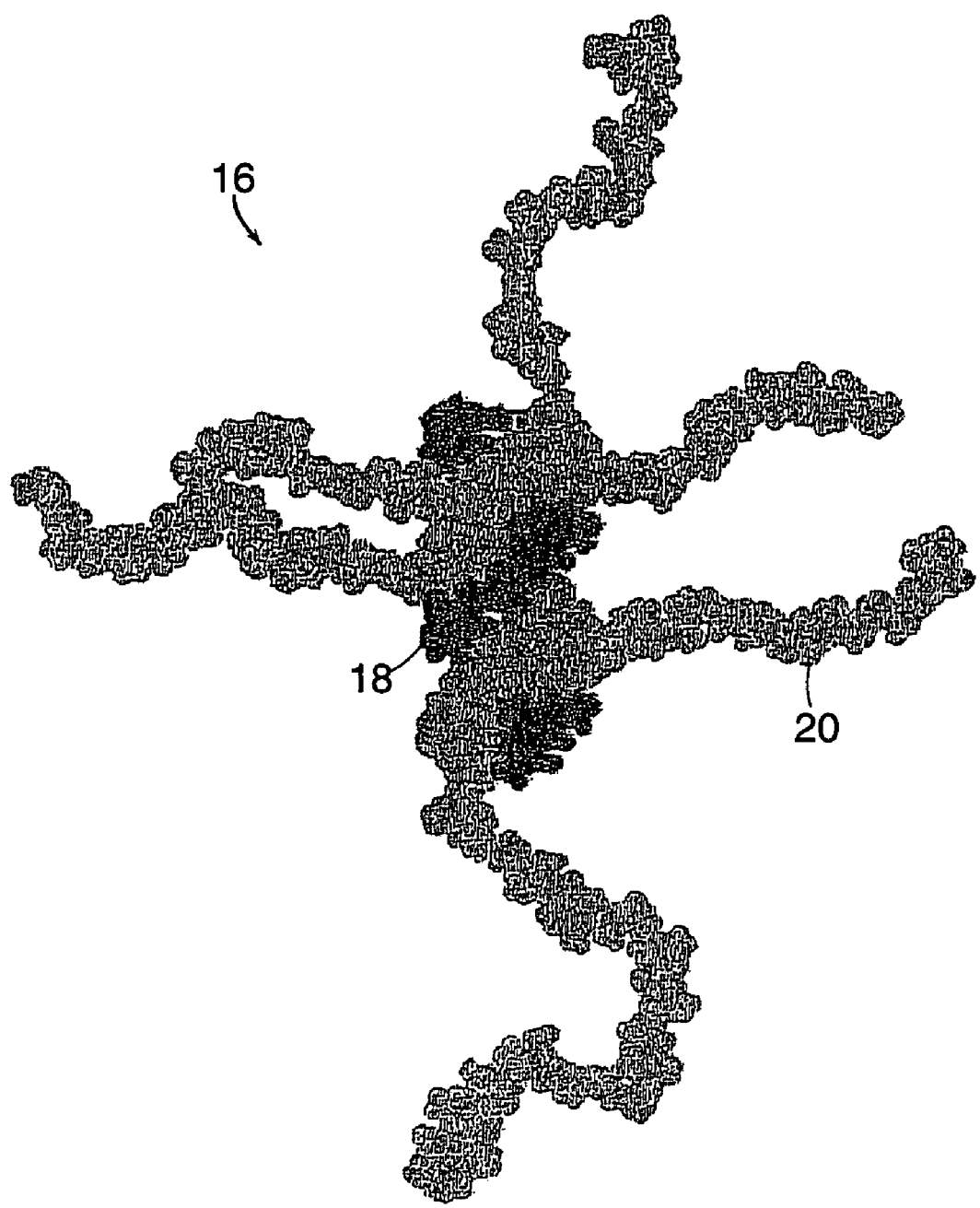
FIG. 2 is a diagrammatic representation of a sterically protected embodiment of a drug-carrier complex of the invention.

In another embodiment, shown in FIG. 2, drug complex 16 includes a double-stranded oligonucleotide core 18 that carries a drug (not shown). Polymers 20 are associated, such as by covalent bonding, with oligonucleotide core 18, thereby providing steric protection.

FIGS. 3A through 3E represent additional embodiments of the drug-carrier complexes of the invention. Specifically, FIG. 3A shows micelle 22, that includes drug 24 reversibly associated with double-stranded oligonucleotides 26. Polymers 28 are arrayed radially from double-stranded oligonucleotides 26.

FIG. 3B shows polymer-modified DNA 30, wherein drug 32 is reversibly associated with single- or double-stranded polynucleotide or oligonucleotide 34. Polymers 36 extend from polynucleotide or oligonucleotide 34.

FIG. 3C shows drug-carrier complex 38, wherein polymer backbone 40 is bound to multiple oligonucleotides 42. Drug component 44 is reversibly associated with oligonucleotides 42, and polymers 46 extend from the backbone and sterically protect oligonucleotides 42.

FIG. 3D shows the drug-carrier complex as modified plasmid 48. Drug 50 and polymer 52 are associated with each other, and the drug is reversibly associated with plasmid component 54.

FIG. 3E shows the drug-carrier complex as gel particle 56, wherein oligonucleotides 58 and associated drug molecules 60 are entrapped in gel 62. Polymers 64 extend from gel 62.

The drug-carrier complexes of the invention include at least one drug. For example, a drug-carrier complex can include at least one nucleotide strand reversibly associated with an oligonucleotide drug (e.g., a ribozyme, an antisense oligonucleotide), an antibacterial drug and a metal containing substance (e.g., platinum, cis-platinum, carboplatin, platinum, gold, silver). The drug-carrier complexes of the invention may be employed to deliver drugs which suppress, or inhibit or otherwise modulate transcription of certain genes, such as growth-related genes in cancers.

In one embodiment, the drug of the drug-carrier complex is combined with at least two nucleotide strands which hybridize with each other in the drug-carrier complexes of the invention.

Additionally, or alternatively, a second nucleotide strand is combined with the drug-carrier complex. In one embodiment, the second nucleotide strand hybridizes with at least one of the nucleotide strands of the drug-carrier complex. The second nucleotide strand may be, as described above for the nucleotide strand of the drug-carrier complex, one or more nucleotides, single stranded, double stranded, DNA, RNA, naturally occurring or synthetic nucleotides.

In another embodiment, the invention relates to a method of forming a drug-carrier complex, comprising the steps of combining a drug with at least two nucleotide strands that hybridize with each other. The drug and nucleotide may be added to a solution (e.g, water) either individually or together. When a drug and nucleotide are combined individually to form the drug-carrier complex, the drug may be added to the solution and then the nucleotide added to the solution or the nucleotide may be added to solution and then the drug added to the solution. Alternatively, the drug and nucleotide may be added to the solution at the same time. In the absence of the hybridized nucleotide strands of drug-carrier complex drug may be either insoluble or have relatively low solubility in water, such as a solubility of less than about one mg/liter at 25° C.

In a preferred embodiment, the dissolved drug-carrier complex is lyophilized. Lyophilization is also referred to as freeze-drying. Methods to lyophilize substances, which can be used to lyophilize the drug-carrier complexes of the invention, are well known in the art. The solution of drug-carrier complex can be frozen (e.g., by placing in a liquid nitrogen or dry ice alcohol bath) and the frozen drug-carrier complex can be placed in a high vacuum. The water (in the form of ice) then vaporizes in the vacuum (sublimation) without melting and the non-water components (dissolved drug-carrier complex) remain in a powder or sponge-like (dehydrated) form.

Another embodiment of the invention is a method of forming a drug-carrier composition, comprising the steps of combining a drug component and a nucleotide component. The combined drug and nucleotide components are lyophilized to form the drug-carrier composition. In a preferred embodiment, at least one of the drug components (e.g., an antisense oligonucleotide, anthracycline, distamycin) and the nucleotide component (e.g., single stranded DNA or RNA, double stranded DNA or RNA) are dissolved in water prior to combining the components. The remaining components then may be added to the combined drug and nucleotide component.

In yet another embodiment, a drug-carrier composition is formed by a method that includes lyophilizing a drug component, lyophilizing a nucleotide component and combining the lyophilized drug component and the lyophilized nucleotide component to form the drug-carrier composition.

In an additional embodiment, the invention relates to a drug carrier that includes a double-stranded nucleotide (e.g., DNA or RNA) and a polymer component covalently bonded to at least one strand of the double stranded nucleotide. The polymer component of the drug carrier has an aqueous solubility of at least one mg/liter at 25° C.

The term "polymer" generally refers to a molecule (e.g., protein, polyether, polyacetal, polysaccharide) formed by the union or bonding of chemically similar or chemically distinct units (e.g., monomers such as amino acids, glucose). Generally, "polymer" refers to a molecule comprising greater than about 30 units. The polymers can be, for example, inorganic polymers such as siloxanes or polyphosphates and derivatives thereof. Alternatively, or additionally, the polymer can be organic. Organic polymers can be natural organic polymers such as polysaccharides, starch, cellulose, pectin, inulin, agarose, chondroitinsulfate, heparin, dextrans, polypeptides (e.g., casein, albumin, globulin, keratin, insulin, polylysine) and derivatives thereof. Organic polymers can be synthetic organic polymers such as polyacetals, polyacrylates, polyvinyl alcohol, polyvinylpyrrolidone, polyethylene glycol, polyesters, polyamides, polyamines and derivatives thereof. Organic polymers may be semisynthetic organic polymers such as methylcellulose, modified starches and derivatives thereof.

In one embodiment, the polymer component of the drug carrier is a biocompatible polymer component. The term "biocompatible," as used herein, refers to a polymer that does not invoke an adverse reaction (e.g., immune response) from an organism (e.g., a mammal), a tissue culture or a collection of cells, or if the adverse reaction does not exceed an acceptable level. In a more preferred embodiment, the biocompatible polymer component is selected from the group consisting of a polysaccharide (e.g., poly α-D-glucose, polysialic acid, dextran, chondroitinsulfate, starch), a polyether and a polyacetal (e.g., poly[hydroxymethylethylene hydroxymethylformal]).

In another embodiment, the biocompatible polymer is cross-linked.

The polymer component of the drug carrier may be one or more chemically similar polymers (e.g., polysaccharide polymer:polysaccharide polymer, polypeptide polymer:polypeptide polymer) or chemically distinct polymers (e.g., a polysaccharide polymer and a polypeptide polymer; a polyether polymer and a polyacetal polymer; a polysaccharide polymer, a polypeptide polymer, and a polyether polymer). In one embodiment, the polymer component of the drug carrier includes at least one polymer covalently bonded to at least one strand of the nucleotide. In another embodiment, the polymer component includes at least two chemically similar or chemically distinct polymers.

An additional embodiment of the invention relates to a drug carrier, comprising a double-stranded nucleotide and an oligomer component covalently bonded to at least one strand of the double-stranded nucleotide.

The term "oligomer," as used herein, refers to a molecule formed by the union or bonding of chemically similar or chemically distinct units (e.g., monomers such as amino acids, glucose, galactose), generally comprising less than about 30 units. Similar to polymers, oligomers can be, for example, inorganic oligomers or organic oligomers. Organic oligomers can be natural organic oligomers, synthetic oligomers or semisynthetic organic oligomers.

The oligomer component of the drug carrier may include at least one oligosaccharide, or at least one oligopeptide, or a combination of both an oligosaccharide and an oligopeptide. In one embodiment, the oligomer component includes at least one oligomer covalently bonded to at least one strand of the nucleotide. In another embodiment, the oligomer component includes at least two oligomers. In yet another embodiment, the oligomer component of the drug carrier includes at least two chemically distinct oligomers. In still another embodiment, the oligomer component of the drug carrier includes at least two chemically similar oligomers.

In another embodiment, the invention is a drug-carrier complex, that includes a single-stranded nucleotide, a polymer and a drug. The drug is reversibly associated with the single-stranded nucleotide. In one embodiment, the polymer is associated with the single-stranded nucleotide. In another embodiment, the polymer is associated with the drug.

In still another embodiment, the invention is a drug-carrier complex, that includes a single-stranded nucleotide, an oligomer and a drug. The oligomer is associated with the single-stranded nucleotide. The oligomer is associated with the single-stranded nucleotide by a covalent association. The oligomer can be associated with the drug. In one embodiment, the drug us reversibly associated with the single-stranded nucleotide. In another embodiment, the drug is reversibly associated with the oligomer.

In an additional embodiment, the invention is a drug carrier that includes a single-stranded nucleotide and at least two polymers associated (e.g., reversibly, irreversibly) with the single-stranded nucleotide. In one embodiment, the chemical association (e.g., reversible, irreversible) between the polymer and the single-stranded nucleotide is a covalent bond. In another embodiment, the chemical association (e.g., reversible, irreversible) between the polymer and the single-stranded nucleotide is a noncovalent bond.

In another embodiment, the invention is a drug carrier that includes a single-stranded nucleotide and at least two oligomers associated with the single-stranded nucleotide. In one embodiment, the chemical association between the oligomer and the single-stranded nucleotide is a covalent bond. In another embodiment, the chemical association between the oligomer and the single-stranded nucleotide is a noncovalent bond.

In yet another embodiment, the invention relates to a drug-carrier composition comprising a nucleotide carrier component and a drug component. The drug-carrier composition has a moisture content less than about 5% by weight.

An additional embodiment of the invention relates to a drug-carrier composition consisting essentially of a drug component and a nucleotide component, wherein other components, such as water or water vapor, essentially are absent.

In another embodiment, the invention relates to a pharmaceutical formulation, that includes a nucleotide carrier component and a drug in reversible association with the nucleotide carrier component. The reversible association of the drug and nucleotide carrier component is as described above for the drug and the nucleotide of a drug-carrier complex and may include, for example, van der Waals force, an electrostatic interaction, a hydrogen bond, an ionic bond, a hydrophobic interaction or a donor/acceptor bond.

The reversible association between the drug and the nucleotide carrier component of the pharmaceutical formulation may include at least one reversible association selected from the group consisting of a van der Waals force, an electrostatic interaction, a hydrogen bond, an ionic bond, a hydrophobic interaction and donor/acceptor bond. The reversible association also may include intercalation between the drug and the nucleotide carrier component. The reversible association between the drug and the nucleotide carrier component of the pharmaceutical formulation can further include a reversible covalent bond between the drug and the nucleotide carrier component.

In one embodiment, the nucleotide carrier component of the pharmaceutical formulation is a polynucleotide carrier component. In another embodiment, the nucleotide carrier component of the pharmaceutical carrier component is an oligonucleotide carrier component.

The drugs that are used in the pharmaceutical formulation are as described above, for example, in drug-carrier complexes of the invention. For example, the drug in the pharmaceutical formulation may be an oligonucleotide drug (e.g., an oligonucleotide, an antisense oligonucleotide or a ribozyme). The drug can include a component selected from the group consisting of an intercalator, a metal containing substance (e.g., platinum, cis-platinum, carboplatin, platinum, gold, silver), a minor groove binder or a major groove binder. In yet another embodiment, the drug includes at least one amino group. For example, the drug doxorubicin includes an amino group.

In still another embodiment, the drug of the pharmaceutical formulation is a protein or a peptide comprising two or more amino acids. The amino acids of the protein or peptide drug can be naturally occurring L-amino acids, D-amino acids, nonnaturally occurring amino acids or synthetic amino acids such as gamma amino acids and cyclic amino acids. The proteins can be post-translationally modified (e.g, glycosylated, myrisilated, acetylated). The N-terminus amino group, the C-terminal carboxyl group, or one or more of the peptide bonds in the protein can be, for example, a non-amino linkage.

In yet another embodiment, the drug of the pharmaceutical formulation includes a diagnostic label. The phrase "diagnostic label," when referring to a drug in the pharmaceutical formulation of the invention, refers to a detectable label incorporated into the drug. The label is used to determine the concentration of the drug, or a drug metabolite, in a certain sample, liquid, organ, tissue, combination of cells, single cell, cell organelle, or elsewhere. Labels include, for example, a radionuclide, a fluorophore, a chromophore, a paramagnetic ion or moiety, a superparamagnetic nanoparticle, a barium or other heavy metal ion, a heavy metal (e.g., gold) particle, an iodine atom, an enzyme, or biotin. The label can be detectable in vitro or in vivo, for example, by radioactivity measurement, gamma scintography, positron emission tomography, nuclear magnetic resonance spectroscopy, magnetic resonance imaging, fluorescence spectroscopy, photoimaging, X-ray (computed) tomography, electron microscopy, enzyme essay, or other respective methods. The information on the label location or content can be used to determine the pathways of drug transfer and metabolization. The diagnostic label also can be used to confirm the presence of a disorder or a disease.

An additional embodiment of the invention relates to a method of delivering a drug to an organism, comprising administering a nucleotide carrier-drug complex to the organism. The nucleotide carrier-drug complex includes a nucleotide carrier and a drug in reversible association with each other. In one embodiment, the reversible association of the drug and the nucleotide carrier component, used in the method of delivering a drug to an organism, is selected from the group consisting of a van der Waals force, an electrostatic interaction, a hydrogen bond, an ionic bond, a hydrophobic interaction and donor/acceptor bond. In another embodiment, the reversible association of the drug and the nucleotide carrier component used in the method of delivering a drug to an organism is an intercalation.

In a preferred embodiment, the organism to which the drug is delivered using the method of the invention is selected from the group consisting of a mammal and a cell. The mammal may be, for example, a primate (e.g., human, rhesus monkey), rodent (e.g., hamster, mouse, rat), ruminant (e.g., sheep, horse, cow) or domestic (e.g., cats, dogs) mammal. The cell may be a procaryotic cell or eucaryotic cell.

In one embodiment of the method of delivering a drug to an organism, the drug-carrier complex is administered into the organism by, for example, systemic or local administration. In another embodiment of the method, the drug-carrier complex is administered proximate to the organism. "Proximate to the organism," as used herein, means near the organism. For example, if the organism is a cell, then the nucleotide carrier may be administered into the cell culture media.

In an additional embodiment, the invention relates to a method of delivering a drug to a tissue culture or a combination of cells (e.g., tissue sample), comprising administering a nucleotide carrier-drug complex to a tissue culture. The nucleotide carrier-drug complex includes a nucleotide carrier and a drug in reversible association with each other. As described above for the method of delivering a drug to an organism, the reversible association of said drug and said nucleotide carrier is selected from the group consisting of a van der Waals force, an electrostatic interaction, a hydrogen bond, an ionic bond, a hydrophobic interaction and donor/acceptor bond. The reversible association between the drug and the nucleotide carrier component in the method can be an intercalation. The drug-carrier complex may be administered into the tissue culture or a combination of cells. Alternatively, or additionally, the nucleotide carrier can be administered proximate to the tissue culture or a combination of cells.

Methods of delivering a drug to a tissue culture described herein can be employed to screen or select drugs which have a particular effect on a particular cell or tissue. For example, drugs of the nucleotide carrier-drug complex can be assessed to determine whether the drug inhibits cellular proliferation of tissue culture cells, or a pathogen such as: normal or cancer cells (e.g., melanoma, mammary adenocarcinoma cell line 293, tissue bioptates), viruses (e.g., HIV, Hepatitis C); bacteria, fungi and protozoa.

Another embodiment of the invention is a method of delivering a drug to an organism, comprising the step of administering a drug and a nucleotide carrier, which reversibly associates with the drug to form a nucleotide carrier-drug complex, to the organism. In one embodiment, the drug and the nucleotide carrier are administered simultaneously to the organism. In another embodiment, the drug and the nucleotide carrier are administered separately to the organism. When the drug and the nucleotide are administered separately to the organism, the drug may be administered first, followed by the nucleotide carrier, or the nucleotide carrier may be administered first, followed by the drug.

In yet another embodiment, the invention relates to a method of delivering a drug to an organism, comprising forming a nucleotide carrier-drug complex that includes a drug and a nucleotide carrier in reversible association with the drug, and administering the nucleotide carrier-drug complex to the organism.

In still another embodiment, the invention relates to a method of delivering a drug to an organism, comprising administering to the organism a drug-carrier complex. The drug-carrier complex includes a drug component and a carrier component in reversible association with each other. The drug dissociates from the drug-carrier complex and reassociates with the carrier component. The degree of association and dissociation can depend, for example, on the concentration of the drug and the carrier, and can be assessed using uv/vis spectroscopy, fluorescent spectroscopy, NMR or other suitable methods. In a preferred embodiment, the carrier component is a nucleotide carrier component. The nucleotide carrier component can be an oligonucleotide or a polynucleotide. The nucleotide carrier component can be a single stranded nucleotide, a double stranded nucleotide, DNA, RNA, naturally occurring or synthetic nucleotides.

In a preferred embodiment, the drug-carrier complex, employed in the method of delivering a drug to an organism, is delivered to a combination of cells in said organism. The combination of cells may be, for example, a cancer (e.g., breast cancer, brain cancer, prostate cancer, lung cancer), a pathogenic organism (e.g., bacteria, virus, fungal), or an organ (e.g., heart, kidney, lung, intestine, stomach).

In one embodiment of the method of delivering a drug to an organism, the drug-carrier complex is administered to an organism and the drug-carrier complex dissociates near or within a combination of cells within the organism. For example, the drug-carrier complex is administered to a human organism and dissociates at or within cancer tissue within the human.

The drug-carrier complex may be administered to the organism at a point remote from the combination of cells of interest. Alternatively, or additionally, the drug-carrier complex may be administered to the organism at a point proximate to the combination of cells of interest. For example, if the combination of cells is lung cancer, administration of the drug-carrier complex via inhalation can be considered administering the drug at a point proximate to the combination of cells. Likewise, if the combination of cells is a small intestine cancer, administration of the drug-carrier complex into the peritoneum is considered to be an administration of the drug at a point proximate to the combination of cells.

The nucleotide carrier-drug complexes and pharmaceutical formulations of the invention may be administered systemically or locally, for example intravenously, intramuscularly, parenterally, orally, nasally, by inhalation, or by suppository. The nucleotide carrier-drug complexes and pharmaceutical formulations of the invention may be administered in a single dose or in more than one dose over a period of time required to achieve a desired effect (e.g., delivery of a drug to a tumor to radiosensitize cancer cells or to decrease or halt cell proliferation).

The nucleotide carrier-drug complexes and pharmaceutical formulations of the invention can be admixed or combined with other pharmaceutical carriers or excipients such as sterile water, salt solutions (such as Ringer's solution), alcohols, or talc to facilitate administration to the organism, tissue culture or combination of cells. The nucleotide carrier-drug complexes and pharmaceutical formulations of the invention can be sterilized and if desired, mixed with auxiliary substances, e.g., cryoprotectors, colorants or preservatives which do not deleteriously react with the nucleotide carrier-drug complexes and pharmaceutical formulations.

It will be appreciated that the actual effective amounts of nucleotide carrier-drug complexes and pharmaceutical formulations of the invention in a specific case may vary according to the specific nucleotide carrier-drug complexes and pharmaceutical formulations being utilized, for example, the mode of administration and the age, weight and disease or disorder of the organism (e.g., a human).

In yet another embodiment, the invention relates to a method for increasing aqueous solubility of a substance, comprising reversibly associating the substance with a nucleotide carrier to form a water-soluble complex. For example, several known bis-intercalators, such as doxorubicin, WP-631, and DMP 840 (Raghavan, K. S., et al., *Pharm. Dev. Technol.* 37:3078-85 (1988), the teachings of which are hereby incorporated by reference in their entirety) have limited solubility at physiological pH. Several substances containing structures that potentially can bind DNA (for example, highly hydrophobic intercalators) remain unstudied because their negligible solubility in aqueous media prevents testing in cell cultures. The phrase "aqueous solubility" generally refers to the ability of a substance to blend (e.g., dissolve) with a water-based solution. The water-based solution can be any solution that contains as one of its components water. For example, the water-based solution can be blood plasma or a physiologically buffered salt solution such as phosphate buffered saline or Ringer's solution. In one embodiment, the substance, without association with the nucleotide carrier, is essentially insoluble in water. The insolubility in water can render the substance inadequate or inefficient for administration to an organism. Thus, increasing the aqueous solubility employing the methods of the invention provides an improved method of delivering drugs to cells, organisms (e.g., mammals) and tissue cultures to treat and study the mechanism of disease and increases the number of compounds that can be used as drugs.

In yet another embodiment, the invention relates to a targeted carrier, comprising a nucleotide, a polymer component associated with the nucleotide and a ligand associated with the nucleotide or the polymer component, and associable with a cell or tissue marker.

The association between the ligand and the nucleotide or polymer component of the targeted carrier can be a reversible (e.g., a van der Waals force, an electrostatic interaction, a hydrogen bond, an ionic bond, a hydrophobic interaction and donor/acceptor bond), a nonreversible association or a covalent bond.

The cell or tissue marker with which the ligand of the targeted carrier associates can be, selected, for example, from the group consisting of proteins, polysaccharides, polypeptides, carbohydrates and lipids. It is to be understood that the terms "proteins," "polysaccharides," "polypeptides," "carbohydrates," and "lipids" are intended to also refer to related compounds, or derivatives, such as glycoproteins, glycolipids, lipopolysaccharides, proteoglycans, lipoproteins, lipid-protein complexes, nucleosomes, and lipoteichoic acids. For example, the cell or tissue marker can be a cell surface receptor such as transmembrane receptor (e.g., G-protein coupled receptors, tyrosine kinase receptors, growth factor receptors). The ligand of the targeted carrier may be selected to specifically target the targeted carrier to a particular cell or tissue to, for example, deliver a drug to treat a disease condition or to compensate for a deficiency.

Tissue markers can be divided, for example, in two major groups. One group can comprise of molecules expressed exclusively or almost exclusively on the surfaces of pathological cells or in the pathological extracellular matrix, or in certain combinations of cells (cell types, cell classes, organs, or tissues). Another group can comprise molecules that are not unique to the pathological sites, but are overexpressed in the pathological sites. Examples of suitable ligands that associate with the cell or tissue marker are platelet-derived growth factor (PDGF), macrophage colony-stimulating factor and epidermal growth factor.

The typical representatives of the first group are asialofetuin receptors (hepatocytes), viral antigens (cells infected by herpes or other viruses), scavenger receptors (macrophages), HER-2/neu (some breast cancer types). The second group includes markers typical for several types of inflammation and cancer, for example, cytokine receptors, receptors of growth factors, surface glycolipids and glycoproteins, integrins, selectins, etc. For example, malignant epithelial cells in primary human lung carcinomas coexpress in vivo PDGF (ligand) and PDGF receptor (cell or tissue marker) (Antoniades, H. N., et al., *Proceedings of the National Academy of Sciences*, 89:3942-6 (1992), the teachings of which are hereby incorporated by reference in their entirety); macrophage colony-stimulating factor (ligand) and its receptor (cell or tissue marker) are expressed in ovarian and endometrial carcinomas (Baiocchi, G., et al., *Cancer*, 67:990-6 (1991), the teachings of which are hereby incorporated by reference in their entirety); coexpression of HER-2/neu and the epidermal growth factor receptor (cell or tissue marker) has been observed in 65% of epithelial ovarian cancers and in a limited number of normal tissue from a fraction of donors (Bast, R. C., Jr., et al., *Cancer*, 71:1597-601 (1993), the teachings of which are hereby incorporated by reference in their entirety); cellular expression of Fuc-GM1 generally was seen together with NCAM in lung carcinomas (Brezicka, F. T., et al., *Tumour Biology*, 13:308-15 (1992), the teachings of which are hereby incorporated by reference in their entirety); thrombospondin-1 is codistributed with CD51 in most of the invasive lobular breast carcinoma cells (40 to 80%) and with CD36 in a subpopulation (30 to 40%) of these cells (Clezardin, P., et al., *Cancer Research*, 53:1421-30 (1993), the teachings of which are hereby incorporated by reference in their entirety); both H-2 and Le(y) were coexpressed in the same individual colorectal carcinoma cells in 92% of cancers expressing both these blood group antigens (Cooper, H. S., et al., *Am. J. Pathol.*, 138:103-10 (1991), the teachings of which are hereby incorporated by reference in their entirety); uPAR and plasminogen activator inhibitor-1 were overexpressed in invasive breast cancer in comparison with normal and benign breast tissues (Costantini, V., et al., *Cancer*, 77:1079-88 (1996), the teachings of which are hereby incorporated by reference in their entirety); coexpression of at least two of cytokeratin, neurofilament, vimentin, and desmin was found in pulmonary neoplasms, whereas in normal tissues these have a different and non-overlapping distribution (Gatter, K. C., et al., *J. of Clinical Pathology,* 39:950-4 (1986), the teachings of which are hereby incorporated by reference in their entirety); the majority of cases of childhood medulloblastoma expressed two or more receptor proteins of EGFR family members (EGFR, HER2, HER3, and HER4); coexpression of the HER2 and HER4 receptors occurred in 54% (Gilbertson, R. J., et al., *Cancer Research,* 57:3272-80 (1997), the teachings of which are hereby incorporated by reference in their entirety); coexpression of multiple (three or more) mucin core proteins occurred in 15 of 25 (60%) advanced (stages III and IV) cancers compared with 1 of 8 (12.5%) early (stages I and II) cancers in gastric adenocarcinomas (Ho, S. B., et al., *Cancer Research,* 55:2681-90 (1995), the teachings of which are hereby incorporated by reference in their entirety); in colorectal cancer, EGFR positive malignant tumors showed coexpression of IL-4 receptor (Kaklamanis, L., et al., *Brit. J. of Cancer,* 66:712-6 (1992), the teachings of which are hereby incorporated by reference in their entirety); overexpression of p53 protein correlated closely with the overexpression of c-erbB-2 in malignant salivary gland tumors (Kamio, N., et al., *Virchows Archiv.,* 428:75-83 (1996); epidermal growth factor receptor EGF-R and C-erbB-2 have been shown to be expressed in human tumors and in some cases relate to the histological grade of the lesions and clinical outcome (Lakshmi, S., et al., *Pathobiology,* 65:163-8 (1997), the teachings of which are hereby incorporated by reference in their entirety); colocalization of MMP-9 was seen with high molecular weight melanoma-associated antigen, the pericyte marker, in ductal breast cancer (Nielsen, B. S., et al., *Lab. Investigation,* 77:345-55 (1997), the teachings of which are hereby incorporated by reference in their entirety); distribution of laminin-5-positive budding cancer cells at the invasion front in colon adenocarcinomas was identical to that of the receptor for urokinase-type plasminogen activator (Pyke, C., et al., *Cancer Research,* 55:4132-9 (1995), the teachings of which are hereby incorporated by reference in their entirety), etc.

Another embodiment of the invention is a targeted carrier that includes a nucleotide and a polymer. The polymer component of the targeted carrier is a ligand associable with a cell or tissue marker. The cell or tissue marker is selected from the group consisting of proteins, polypeptides, carbohydrates, lipids and nucleotides and derivatives thereof. A cell or tissue marker can also be a glycolipids, glycoproteins, glycopeptides, transmembrane proteins, glycoproteins and proteoglycans of the extracellular matrix and other molecules present in tissues and exposed to the extracellular environment. This also includes intracellular components exposed to the extracellular environment in disease (e.g., nucleosomes).

In yet another embodiment, the invention is a targeted drug-carrier complex, comprising a nucleotide, a drug reversibly associated with the nucleotide and a targeting component. The targeting component is associated with the nucleotide or the drug. The targeting component includes a ligand associable with a cell or tissue marker. The ligand can be, for example, associable with the cell or tissue marker by covalent, noncovalent or reversible associations The cell or tissue marker is selected from the group consisting of proteins, polypeptides, carbohydrates, lipids and nucleotides. The drug is reversibly associated with the nucleotide. The targeting component is associated either with the drug or with the nucleotide.

In still another embodiment, the invention is a targeted drug-carrier complex that includes a nucleotide, a drug reversibly associated with the nucleotide, a polymer component and a targeting component. The polymer component is associated with the nucleotide or the drug. The targeting component is associated with the nucleotide, the drug or the polymer. The association between the targeting component and the drug or polymer can be, for example, a covalent bond, noncovalent bond or a reversible association. The targeting component includes a ligand associable with a cell or tissue marker and a drug. The association between the targeting component and the ligand can be, for example, a covalent bond, noncovalent bond or a reversible association. The cell or tissue marker is selected from the group consisting of proteins, polypeptides, carbohydrates, lipids and nucleotides.

Figure 4:
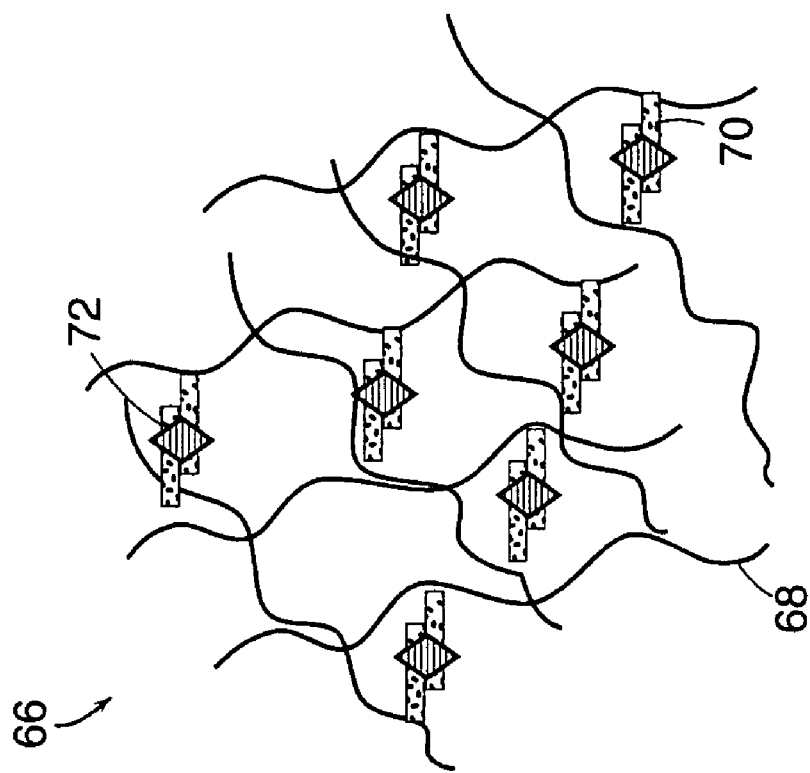
FIG. 4 shows a schematic representation of a method of forming a drug delivery system of the invention by combining a drug with a gel matrix crosslinked through nucleotide strands that hybridize with each other.
Figure 4:
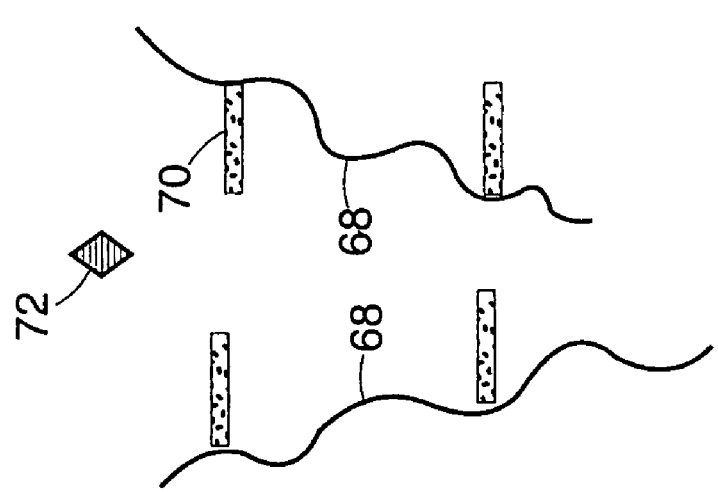

In an additional embodiment, the invention relates to a drug delivery system, comprising a matrix, a nucleotide associated with or entrapped within the matrix, and a drug in reversible association (e.g., a van der Waals force, an electrostatic interaction, a hydrogen bond, an ionic bond, a hydrophobic interaction and donor/acceptor bond) with the nucleotide (FIG. 4).

In a preferred embodiment, the matrix of the drug delivery system is a gel, a film or a particle. The matrix provides a structural foundation of the drug delivery system. Additionally, the matrix can minimize any adverse reaction an organism, cell or tissue culture may have to the drug delivery system. Preferably, the matrix is biocompatible.

Matrix materials generally are selected in accordance with the method of administration of the drug release system. In topical systems, such as gels, films, patches and other systems for external application, hydrophilic gels frequently are used as matrix materials. Gels are made, for example, of biocompatible polymers such as collagen, fibrin, polyvinylpyrrolidone, polyvinyl alcohol, polyethyleneglycol, polypropyleneglycol, polyacrylates, or combinations thereof. Other systems, such as liniments, include emulsions, suspensions, and liposomal preparations, sometimes in mixtures with each other or entrapped within a gel. Systems for internal use are often engineered on the basis of either injectable gels (e.g., polyethyleneglycol), or biodegradable sutures (e.g., copolymers of lactic and glycolic acid). Implantable drug delivery systems are described below as implants.

Generally, it is preferable that the matrix of the drug release system remains stable for as long as the drug release system remains functional, e.g., for as long as the drug is being released at a desirable rate. In some cases, it would be preferable that, after the drug essentially has been released, the structural matrix of the drug release system would disintegrate rapidly. In an embodiment of the invention, this effect is achieved by matrix stabilization by the drug. In a preferred embodiment, the matrix of the drug release system 66 (e.g., a hydrophilic polymer gel in FIG. 4) is reversibly crosslinked via cross-hybridization of short oligonucleotides 70 chemically associated (e.g., covalently bound) with the matrix material 68 (FIG. 4). Preferably, melting temperature of the double-stranded links formed as a result of hybridization is near or below normal body temperature. Association of a drug 72 with the double-stranded oligonucleotide stabilizes the latter and increases the melting temperature, making the gel stable at body temperature (FIG. 4). Drug release results in the decrease of the melting temperature of the oligonucleotide links, which destabilizes the matrix (increases the rate of matrix dissolution, biodegradation or bioresorption).

In still another embodiment, the invention relates to an implant, comprising an implant matrix, a nucleotide associated with or entrapped within the matrix, and a drug in reversible association (e.g., a van der Waals force, an electrostatic interaction, a hydrogen bond, an ionic bond, a hydrophobic interaction and donor/acceptor bond) with the nucleotide.

Implants capable of sustained drug release (implantable drug delivery systems) can be useful, for example, for prolonged systemic delivery of a drug after a single administration, for drug delivery to local lymph nodes draining the implantation site, or for postoperative local wound treatment. The implant can be made, for example, of a solid material or a gel, and can be made as a single block (tablet, film) or consist of multiple particles. Alternatively, the structural foundation of the implant can be engineered as a sponge, foam, fabric, thread, or otherwise.

The implant can be of any size and shape suitable for implantation. Particulate, thread or film implants can be more suitable for minimally invasive methods (such as implantation through a needle or other surgical tool), whereas other types of implants may be more suitable for conventional surgery.

General requirements to the implantable materials and devices are the following: simple, minimally invasive application, calibrated magnitude and time course of biological effect(s); minimal risk of adverse reactions; minimal monitoring and maintenance, and, in many applications, complete biodegradation after the clinical objectives have been reached. The implants should perform precise biological functions, e.g., mediated by controlled release of biologically active compounds and/or direct structural and functional support of tissues and/or cell cultures, which can be performed best by macromolecular or supramolecular matrices comprising specialized functional domains. Matrices should be stable and biologically inert in vivo for a predetermined period of time, and completely degradable after their function has been completed. The biodegradation should not result in producing any toxic products nor polymer deposition in draining lymph nodes. Examples of implant matrix materials are: silicone, copolymers of lactic and glycolic acids, agarose, porous metals (e.g., titanium), coral matrix, acrylates. Other possible materials include polyethyleneglycol, polyacetals, polysaccharides, denatured or crosslinked proteins (e.g., albumin, gelatin) or natural proteins (e.g., collagen, fibrin). ("Implantation Biology," Greco, R. S., ed. CRC Press, Boca Raton, Fla. (1994); Holmdahl, L., et al., *European Journal of Surgery—Supplement*, 577:56-62 (1997); Karel, I., et al., *Graefes Archive for Clinical & Experimental Ophthalmology*, 235: 186-9 (1997); Mikos, A. G., et al., *Biotechnol. Bioeng.*, 42:716-723 (1993); Wald, H. L., et al., *Biomaterials*, 14:270-278 (1993); Galetti, P. M., *Trans. Am. Soc. Artif. Inter. Organs*, 25:510 (1979); Sheardown, H., et al., *Current Eye Research*, 16:183-90 (1997); Gordon, R. D., et al., *Advances in Surgery*, 21:49-64 (1988); diZerega, G. S., *European Journal of Surgery—Supplement*, 577:10-6 (1997); Fulton, G. J., et al., *Journal of Vascular Surgery*, 25:453-63 (1997); Chandrashekar, G., et al., *Journal of Pharmacy & Pharmacology*, 48:669-74 (1996); Rehman, I. U., *Journal of Biomaterials Applications*, 11:182-257 (1996); Miller, B. H., et al., *Journal of the American Academy of Dermatology*, 36:72-7 (1997); Chowdhury, S. M., et al., *Journal of Surgical Research*, 61:58-64 (1996); Bourke, R. D., et al., *Eye*, 10:501-8 (1996); Rohrich, R. J., et al., *Plastic & Reconstructive Surgery*, 98:552-62 (1996); Gabka, C. J., et al., *Seminars in Surgical Oncology*, 12:67-75 (1996); Raso, D. S., et al., *Journal of the American Academy of Dermatology*, 35:32-6 (1996); Yoshida, S. H., et al., *Life Sciences*, 56:1299-310 (1995); Sanchez-Guerrero, J., et al., *New England Journal of Medicine*, 332:1666-70 (1995); Ahn, C. Y., et al., *Aesthetic Plastic Surgery*, 19:361-7 (1995); Sittinger, M., et al., *Biomaterials*, 15:451-6 (1994); Muzzarelli, R. A., et al., *Biomaterials*, 14:39-43 (1993); Henderson, R., et al., *Spine*, 18:1268-72 (1993); Tal, H., et al., *Journal of Clinical Periodontology*, 23:1-6 (1996); Smith, J. P., et al., *Anti-Cancer Drugs*, 6:717-26 (1995); Nakayama, Y., et al., *ASAIO Journal*, 4:M374-8 (1995); Schuman, L., et al., *Biomaterials*, 16:809-14 (1995); Khare, A. R., et al., *Biomaterials*, 16(7):559-67 (1995); Sawada, Y., et al., *British Journal of Plastic Surgery*, 46:576-9 (1993); Karel, I., et al., *Graefes Archive for Clinical & Experimental Ophthalmology*, 235:186-9 (1997), the teachings of all of which are hereby incorporated by reference in their entirety).

The implant can be designed to release a certain dose of the drug over a particular period of time. In one embodiment, the matrix is a material reversibly cross-linked with a nucleotide/nucleotide association. In another embodiment, the release of the drug from the implant destabilizes the implant matrix.

The invention now will be described further by the following examples, which are not intended to be limiting.

EXEMPLIFICATION

Example 1

Hybridization of Single-Stranded Oligonucleotides

Two custom-synthesized single stranded oligonucleotides, 5' AAA TCT CCC AGC GTG CGC CAT AA 3' (SEQ ID NO: 1) and 5' tt AtG GCG CAC GCt GGG AGA ttt 3' (SEQ ID NO: 2), where t is an amino modified T, were purchased from a commercial source. The oligonucleotides were dissolved, 10 mg/ml each, in 50 mM sodium phosphate buffer solution (PBS) with pH=7. Equimolar amounts of the above solutions were mixed at ambient temperature (25° C.). The resultant solution (total volume 22 µl) was transferred to a capped 1 ml vial, and the vial was heated to a 95° C. in a 100 ml water bath for 10 minutes. Then the bath was allowed to cool down to 25° C. The resultant product, a double-stranded oligonucleotide, was purified by size exclusion HPLC in water and lyophilized. Yield: 91%.

Example 2

Formation and Isolation of Carrier-Drug Complex

An oligonucleotide with arbitrarily chosen 18-base sequence, 5'CGT CGA CGT CGA ATA TAC GC (SEQ ID NO: 3), and a complementary 5'-amino modified oligonucleotide 5'GC GTA TAT TCG ACG TCG ACG (SEQ ID NO: 4) were purchased from a commercial vendor. To form a double stranded oligonucleotide, the single-stranded oligonucleotides were hybridized and lyophilized as described in Example 1. The resultant double stranded oligonucleotide was stable at ambient (25° C.) and body temperature (37° C.).

Doxorubicin was dissolved in water at 0.2 mg/ml at pH=5. The double-stranded oligonucleotide was dissolved in water at 2 mg/ml without pH adjustment. The solutions, 0.1 ml each, were mixed. Subsequently, 0.3 ml of PBS, pH=7, were added, and the resultant solution was incubated at ambient temperature for 10 minutes. After the incubation, the reaction mixture was purified by gel chromatography on Sephadex G-25 in water. Doxorubicin elution was monitored photometrically at 470 nm. Essentially all doxorubicin was found in the oligonucleotide fraction. In a control gel chromatography experiment, no doxorubicin was eluted in the same fraction (see also Example 5). After the gel chromatography, the doxorubicin-oligonucleotide adduct was lyophilized. The lyophilized preparation was found to be readily soluble in water and aqueous media at physiological pH (pH=7 to 8).

Example 3

Drug-Carrier Adduct with High Drug Content

Drug-carrier adduct with a high drug content was prepared essentially as described in Example 2, using the same double stranded oligonucleotide and doxorubicin:oligonucleotide ratio 1:5 (w/w), which corresponds to approximately one doxorubicin molecule per four base pairs. The resultant adduct was purified by gel chromatography (PD-10 column, water) and lyophilized. Yield: 98±2%.

Example 4

Lyophilization and Reconstitution

The adducts obtained as described in Examples 2 and 3 were used in a lyophilized form. Doxorubicin powder (Sigma Chemical Co., St. Louis, Mo.) and lyophilized "Doxorubicin for injection" were used as control preparations. Each of the four preparations, in the amount of one milligram by doxorubicin, were suspended in 0.1 ml of a 50 mM PBS, pH=7. Both oligonucleotide adducts immediately dissolved, whereas the two control preparations formed suspensions. The resultant solutions oligonucleotide-doxorubicin adduct solutions were filtered through 0.22 mm PTFE membrane filters; doxorubicin was recovered in the filtrates with at least 98% yield (by adsorption at 470 nm). Filtration of the suspensions of the control preparations through 0.22 mm PTFE membrane resulted in the recovery of less than 5% of doxorubicin in the filtrate; the rest was retained by the filter.

Example 5

Doxorubicin Interation with Sephadex G-25

Doxorubicin solution, 0.1 ml of a 0.1 mg/ml solution, was applied to a short column packed with Sephadex G-25 (PD-10, Pharmacia). Formation of doxorubicin-Sephadex adduct was detected by formation of a characteristically colored red layer. Elution with water resulted in 0% doxorubicin recovery in the first 10 ml, with subsequent slow elution. Analogous experiment with doxorubicin adducts with model carrier (Examples 2, 3) resulted in complete doxorubicin elution in a 2.5 ml fraction (2.5 to 5.0 ml).

In a subsequent experiment, doxorubicin was adsorbed on the PD-10 column as described above, and the column was washed with 10 ml $H_2O$. Then the double-stranded oligonucleotide of Example 2, 0.1 ml of a 1 mg/ml solution, was passed through the same column. Doxorubicin adsorbed on Sephadex G-25 was completely desorbed from the column, and eluted within the oligonucleotide fraction (2.5 to 5.0 ml).

Example 6

Electrophoreseis of Doxorubicin Adducts with Model Drug-Carrier Complexes

Electrophoretic mobility of the adducts of Examples 2 and 3 were studied in 0.8% horizontal agarose gel, 0.47 kV/m, 0.01 M Tris-HCl buffer, pH=8. Doxorubicin was used as a control. As determined by doxorubicin fluorescence, doxorubicin adducts and free doxorubicin migrated in opposite directions.

Example 7

Carrier Modification with Polymer (Steric Protection)

To determine the degree of steric protection of the nucleotide core by polymer chains, a series of double-stranded oligonucleotides were synthesized. A model antigen (fluorescein) and a model protective chain (polyethyleneglycol) were positioned on the oligonucleotide at various distances. Then kinetics of fluorescein moiety interactions with fluorescence-quenching antifluorescein rabbit IgG (Molecular Probes, Oreg.) was determined to evaluate the degree of steric protection. The latter was investigated as a function of the distance between the antigen and the protective chain. Four 5'-amino modified oligonucleotides with the same sequence 5'-TTT-CTC-TCT-CTC-TCT-CTC-TCT-3' (SEQ ID NO: 5) were obtained from a commercial source. Oligonucleotides were additionally modified during the synthesis with fluorescein at either the 2-nd, 9-th, 16-th or the 20-th base from the 5' end. These oligonucleotides (first strand) were hybridized with a complementary oligonucleotide, 5'-AGA-GAG-AGA-GAG-AGA-GAG-AAA-A-3' (SEQ ID NO: 6) (second strand), essentially as described in Example 2.

The resultant double-stranded oligonucleotides were purified by SEC HPLC and modified, through the 5'-aminogroup of the first strand, with N-hydroxysuccinimide ester of carboxy-polyethyleneglycol (MW=2 kDa and 20 kDa), and with N-hydroxysuccinimide ester of branched "PEG2" polyethyleneglycol (10 kDa). All polymers were purchased from Shearwater Polymers, Inc. The resultant conjugates were purified by SEC HPLC. Solutions with approximately equal (1±0.1 nM) oligonucleotide concentration were prepared in 20 mM PBS, pH=7.5. Anti-fluorescein IgG was added at 10-fold concentration to ensure pseudo first order conditions. Fluorescein—antibody interaction was registered by quenching of the fluorescein fluorescence by the antibody. Fluorescence was registered at 515 nm (excitation at 490 nm). The kinetics of fluorescence quenching depended on the position of the fluorescein moiety relative to the polymer chain.

Polymer chains positioned at 16-20 bases did not attenuate fluorescein-antibody interaction, whereas polymer chains positioned within 2 and 9 bases did decrease the kinetic constant by 20% (2 kDa polymer) to 80% (20 kDa polymer). Thus, the degree of steric protection of the nucleotide can be optimized via optimization of the distance between polymer chains (number of chains per base pair) and of the molecular weight of the polymer. Based on the data described in the following examples, a 50% to 80% hindrance of the carrier core (as measured by protein access kinetics) can be sufficient to prolong carrier circulation by several hours.

Example 8

Model Sterically Protected (Polymer-Modified) Carriers

Two model carriers were prepared for biological studies. Complementary oligonucleotides with sequences 5'-ATG-GCG-CAC-GCT-GGG-AGA (SEQ ID NO: 7) and 5'-TCT-CCC-AGC-GTG-CGC-CAT-c (SEQ ID NO: 8) (lower case letter "c" indicates an RNA base) were custom-synthesized. One carrier was prepared using unmodified oligonucleotides, essentially as described in Example 2. Another was prepared using 5'ATG-GCG-CAC-GCT-GGG-AGA-c (SEQ ID NO: 9) amino modified at 1-st, 2-nd, 12-th and 19-th positions, counting from the 5' end of the oligonucleotide. Oligonucleotides were hybridized in water at pH=7, total oligonucleotide concentration 1 mg/ml and purified by HPLC. Amino modified carrier was modified with 10 kDa poly(hydroxymethylethylene hydroxymethylformal) (PHF) containing 20% aldehyde groups. The latter polymer was prepared via oxidation of Dextran B512 with 1.8 periodate molecules per carbohydrate ring, with subsequent borohydride reduction and second periodate oxidation of the resultant glycol groups. Aldehydo-PHF (50-fold excess) was reacted with the amino modified carrier core in the presence of cyanoborohydride (1 mole per mole aldehyde) overnight at ambient temperature. The product (oligonucleotide-PHF conjugate) was isolated by SEC HPLC. Both carriers were lyophilized.

Example 9

Drug-Carrier Complex Conjugation with Model Antibody

A PHF-modified carrier, analogous in structure to the carrier of Example 8 but comprising glycol groups in the polymer chains, was prepared using a modified technique. The amino modified carrier was modified with 10 kDa poly(hydroxymethylethylene hydroxymethylformal) (PHF) containing 10% aldehyde groups and 10% glycol groups. The latter was prepared by incomplete periodate oxidation of the same polymer as in Example 8 (prepared via oxidation of Dextran B512 with 1.8 periodate molecules per carbohydrate ring, with subsequent borohydride reduction). The carrier (0.1 mg) was treated with 1 ml of 10 mM periodate for 5 minutes, purified on PD-10 column, and conjugated with rabbit anti-fluorescein IgG (0.01 mg) (Molecular Probes, Oreg.) by overnight incubation in the presence of 0.1 mg/ml sodium cyanoborohydride at pH=8, 25° C. The conjugate was separated from the unreacted IgG by HPLC (yield by IgG absorption at 280 nm: 22±9%). The presence of active IgG in the conjugate was determined by quenching of fluorescein fluorescence (10 nM fluorescein, pH=8, 25° C.). The calculated amount of active IgG in the carrier was 1±0.3% w/w.

Example 10

Carrier Conjugation with Lactose

An amino modified carrier prepared as in Example 8 was modified with trace amounts of diethylenetriaminepentaacetic anhydride in 10 mM PBS, pH=8. The product was conjugated with lactose via 48 hr incubation at pH=8, at 10 mg/ml of each the carrier and lactose, in the presence of 1 mg/ml sodium cyanoborohydride. The product was isolated by HPLC.

Example 11

Drug-Carrier Adduct Modification with PHF Via (Aminooxy)Doxorubicin

An aminooxy-derivative of doxorubicin, N-(3-aminooxy-2-hydroxypropyl)-doxorubicin (AHD), was synthesized via doxorubicin reaction with N-oxyranylmetoxy)ethanamidic acid ethyl ester, with subsequent treatment of the product with 2N HCl. The product was purified by thin layer chromatography. Carrier loading with AHD was made as in Example 2. The resultant adduct was incubated with aldehydo-PHF (polymer described in a Example 8) at pH=6.5, 25° C., 24 hr. The conjugate was isolated by SEC HPLC (BioRad BioSil 125 column). Adduct modification with polymer chains was detected by decrease in the elution time of the adduct (6.2 min vs. 8.5 min for unmodified adduct). In a control experiment, polymer incubation with analogous unloaded carrier, the elution time of the latter remained unchanged.

Example 12

Carrier Loading with Radiolabeled Doxorubicin $^{14}$C labeled doxorubicin (Amersham, 2.00 GBq/mmol), 25 mCi, was dissolved in 100 ml water. Then 10 ml of this solution were mixed with 0.25 ml of 2 mg/ml unlabeled ("cold") doxorubicin. Carriers of Example 8 were dissolved in water (11 mg/ml by nucleotide core), and mixed with a calculated amount of doxorubicin solution to obtain adducts with 1 Doxorubicin molecule per 10 base pairs. After a 10 min incubation, the adducts were purified on Sephadex G-25 and lyophilized. Analogous complex was prepared with high molecular weight DNA (polyC/PolyG, Sigma Chemical Co, St. Louis, Mo.). Analogous cold (unlabeled) preparations were prepared using unlabeled doxorubicin.

Example 13

Toxicity

Carrier toxicity in cell culture. Unloaded carriers (Example 7) were tested in near confluent culture of human epithelial cells (kidney, line 293, from ATCC #CRL 1573) in DMEM with 5% calf serum. Carriers were added to the cell culture at various concentrations, from 1 mg/ml to 1 mg/ml. Cell survival rate was determined by staining with Trypan Blue after a 16-hour incubation. No detectable cell toxicity was found at all carrier concentrations.

Adduct toxicity in cell culture. Doxorubicin-loaded carriers (Example 12) were tested in near confluent and growing cultures of human epithelial cells (kidney, line 293) in DMEM containing 5% calf serum. This cell line is relatively resistant to doxorubicin. Cell survival rate was determined by staining with Trypan Blue after a 16-hour incubation. No detectable cell toxicity was found at doxorubicin concentrations up to 2 mM in confluent culture, while in growing culture 15-20% of cells were stained with Trypan Blue at 2 mM. In a control experiment, free doxorubicin showed essentially the same cytotoxic effects. This example shows that association of doxorubicin with nucleotide-based carrier did not increase doxorubicin toxicity for resting cells, and did not suppress cytotoxicity for dividing cells.

Carrier toxicity in vivo. Sterically protected model carrier of Example 8 was injected intravenously, through the tail vein, to anesthetized outbred mice at 100 mg/kg (n=6, male, 31±2 g). Animals were observed for 30 days. None of the animals showed signs of toxicity. All animals survived.

Adduct toxicity in vivo. A sterically protected drug-carrier complex ( ) of Example 8 was loaded with a bis-intercalator WP-631 synthesized via crosslinking of two daunorubicin molecules with αα-Dibromo-p-xylene as described in the literature (Chaires, J. B., et al., *J. Med. Chem.* 40:261-6 (1997), the teachings of which are hereby incorporated by reference in their entirety). Bis-intercalator content was one molecule per 6 base pairs of the nucleotide core. The DNA adducts of this bis-intercalator are highly stable and bis-intercalator release is slow (release half life was 9±1 hr, as measured in 0.9% NaCl, 10 mM PBS, pH=7.5). The adduct and free bis-intercalator were administered intravenously, as described above, into male outbred mice (30±2 g, n=4 per group) at 30 mg/kg by bis-intercalator. In a third group, unloaded carrier was injected at 100 mg/kg within 15 minutes after the administration of 30 mg/kg of bis-doxorubicin.

Mice were observed for 30 days. In the group injected with the free bis-intercalator, only one animal survived, whereas in the group injected with the adduct all animals survived. In the group where bis-doxorubicin administration was followed by carrier administration, all animals survived. These data show that drug association with drug-carrier complexes of the invention decrease toxicity in vivo, likely due to a decreased concentration of free drug in plasma.

Example 14

Carrier Biokinetics

Unloaded carriers (Example 8) were labeled with tritium ($^3$H). Carriers were oxidized with periodate to produce aldehyde groups on the 3'-ribonucleotide base present in the structure, and reacted with [$^3$H] borohydride to introduce tritium into carrier core structure. Carriers were purified on Sephadex G-25 and injected at 1 mg/kg into normal outbred mice (males, 30 g) via tail vein. Blood samples were collected at different time points and counted. The blood half-lives were ca. 30 min and 10 hours for unprotected and PHF-protected carriers, respectively. This example shows that circulation time of the nucleotide-based carriers can be optimized by steric protection, and long-circulating carriers can be prepared via modification with hydrophilic polymers.

Example 15

Doxorubicin Biodistribution ($^{14}$C)doxorubicin-loaded carriers (Example 12) and free ($^{14}$C)doxorubicin (control) were injected into normal outbred mice (males, 30 g) via tail vein, at 0.3 mg/kg. Biodistribution was studied by measuring tissue radioactivity 20 hours after injection. Tissue samples were disintegrated, solubilized, mixed with a scintillation cocktail and counted on a scintillation counter. Although doxorubicin-DNA complex is known to be relatively unstable, significant differences in label accumulation were found.

The administration of doxorubicin as adduct with unprotected oligonucleotide carrier resulted in minimal deviation from the biodistribution of free doxorubicin. The administration of doxorubicin adduct with PHF-protected carrier resulted in twice higher label content in skeletal muscle, 6±2 vs. 2±0.4% dose/g (mean±standard deviation). Doxorubicin adduct with DNA showed increased label distribution to lung (7±3.1% vs. 4.6±1.6% dose/g) and liver (12±6 vs. 3±0.6% dose/g). These data show that biodistribution of an agent that binds DNA can be significantly altered if the agent is administered as an adduct with nucleotide-based carrier. Notably, doxorubicin-DNA association is less stable than of other intercalators. For other, stronger DNA binders, the effect of redistribution can be more significant and, in general, different for each particular combination of a nucleotide-based carrier and a drug substance.

Example 16

Model pCMV-Based Carrier

A plasmid solution in PBS, pH=7.5, 0.1 ml, containing 10 mg/ml pCMV (Promega), was mixed with 10 ml of 1 mg/ml solution of bis-doxorubicin (described in Example 13). After a 1 hr incubation, the adduct was isolated by SEC HPLC (BioRad BioSil 125 column). Bis-doxorubicin association with the plasmid was detected by appearance of absorption at 470 nm in the excluded volume.

Example 17

Model Gel

A hydrophilic polyacetal matrix material (PHF) with 20% aldehyde substitution, MW=250 kDa, was prepared as described in Example 9. 50 mg of the polymer were conjugated with 1 mg of 3'-amino modified oligonucleotide with sequence 5'-ATG GCG CAC-3' in the presence of sodium cyanoborohydride (I mg/ml) in 1 ml of 50 mM PBS, pH=8. Analogously, a conjugate of a complementary 3'-amino modified oligonucleotide with sequence 5'-GTG CGC CAT-3' was prepared. Both oligonucleotides were custom-ordered from a commercial source.

The two conjugates were dissolved in water at 50 mg/ml each and mixed. Immediately after mixing, the viscosity of the mixture rapidly increased. Daunomycin, 0.5 mg in 10 ml DMSO, was added to the mixture. Immediately, the mixture formed a gel, presumably as a result of stabilization of intermolecular double-stranded oligonucleotide linkages via Daunomycin intercalation. A pellet of this gel (disk, d=15 mm, h=5 mm), was incubated under slow stirring in 1 liter of 0.9% NaCl at pH=7.5. Daunomycin release was registered spectrophotometrically. The initial half-release time was found to be 40±12 min.

Example 18

Oligonucleotide Conjugation with Polylysine

5'-amino modified oligonucleotide with sequence 5'-TTT-CTC-TCT-CTC-TCT-CTC-TCT-3' (SEQ ID NO: 10) was hybridized with a complementary oligonucleotide and the product was treated with succinic anhydride at 1 mg/ml (each reagent) in 50 mM PBS, pH=8.5, for 3 hours at ambient temperature. The product was purified by SEC on Sephadex G-25 (PD-10 column). Polylysine hydrobromide, 20 kDa, 0.1 ml of 2 mg/ml solution, was mixed with 0.1 ml of a 1 mg/ml of the oligonucleotide solution in PBS, pH=6. Subsequently, ethyl-(N-dimethylaminopropyl)carbodiimide (EDC), 1 mg in 0.1 ml water, was added to the mixture at 4° C., and the mixture incubated overnight at 4° C. and subsequently for three hours at 25° C. The product was desalted on Sephadex G-25 (PD-10). The conjugate was isolated by SEC HPLC.

Example 19

Steric Protection of Oligonucleotide-Polylysine Conjugate

N-hydroxysuccinimide ester of terminal-carboxypropylthio-PHF was prepared via PHF reaction with mercaptopropionic acid with subsequent modification with N-hydroxysuccinimide in the presence of dicyclohexylcarbodiimide. The conjugate synthesized in Example 18 (ca. 0.1 mg in 1 ml water) was mixed with 0.5 ml of 50 mM borate buffer, pH=8. N-hydroxysuccinimide ester of terminal-carboxypropylthio-PHF, 10 mg, was dissolved in 0.1 ml DMSO. The solutions were mixed and incubated at room temperature overnight. The product was isolated by size exclusion HPLC (BioSil 125 column).

Example 20

Sterically Protected Adduct of a Model Oligonucleotide

An arbitrarily chosen 5-amino modified 18-base phosphodiester oligonucleotide 5° CGTCGACGTC-GAATATACGC (SEQ ID NO: 11), 0.11 mg, was modified with trace amount of ethylenediaminetraacetic anhydride and hybridized with (a) a complementary oligonucleotide, 5'GCGTATATTCGACGTCGACG (SEQ ID NO: 12), and (b) analogous complementary oligonucleotide amino modified at both 5' and 3' ends and at positions 4, 9 and 15 (from 5'). The hybridized amino modified DSO was incubated with 1 ml of 10 mg/ml solution of N-hydroxycuccinimido-polyethyleneglycol, MW=10 kDa, at pH=8 for 8 hours. The products, PEG-modified double stranded oligonucleotides, were isolated by HPLC. Both PEG-modified and unmodified double stranded oligonucleotides were labeled with 111 in 0.5 M citrate buffer solution, pH=5.6. Labeled preparations were purified by SEC HPLC. Each was divided into 4 equal doses and administered intravenously to outbred mice (n=4 in each group, male, 31±2 g). Blood samples were taken immediately after injection, then at 0.25, 0.5, 1, 2, 4 and 8 hours. Blood half-lives of the model oligonucleotides in unmodified and polymer-modified adducts were found to be 12±5 min and 4.5±0.7 hrs, respectively.

EQUIVALENTS

While this invention has been particularly shown and described with references to preferred embodiments thereof, it will be understood by those skilled in the art that various changes in form and details may be made therein without departing from the spirit and scope of the invention as defined by the appended claims.

---

What is claimed is:

1. A pharmaceutical formulation, comprising:
a drug-carrier complex comprising:
(1) a polyacetal polymer, wherein the polyacetal polymer comprises poly(hydroxymethylethylene hydroxymethyl formal);
(2) first single-stranded nucleotide strand that is optionally chemically modified and that is associated with the polyacetal polymer through a covalent bond; and
a second nucleotide strand.

2. The pharmaceutical formulation of claim 1, wherein the second nucleotide strand is a nucleotide strand that has a sequence that is at least partially complementary to that of the first nucleotide strand, such that the second nucleotide strand reversibly binds to the first nucleotide strand.

3. The pharmaceutical formulation of claim 1 or 2, wherein the second nucleotide strand is single-stranded.

4. The pharmaceutical formulation of claim 1 or 2, wherein the drug carrier complex-further comprises a targeting component.

5. The pharmaceutical formulation of claim 4, wherein the targeting component comprises a ligand associated with the first nucleotide strand or with the polyacetal polymer component, and wherein the ligand is associable with a cell marker or tissue marker.

6. The pharmaceutical formulation of claim 5, wherein the association between the ligand and the first nucleotide strand or polyacetal polymer component is reversible.

7. The pharmaceutical formulation of claim 6, wherein the reversible association between the ligand and the first nucleotide strand or polyacetal polymer component includes at least one member selected from the group consisting of a van der Waals force, an electrostatic interaction, a hydrogen bond, an ionic bond, a hydrophobic interaction and a donor/acceptor bond.

8. The pharmaceutical formulation of claim 5, wherein the association between the ligand and the first nucleotide strand or polyacetal polymer component is nonreversible.

9. The pharmaceutical formulation of claim 8, wherein the nonreversible association between the ligand and the first nucleotide strand or polyacetal polymer component is covalent.

10. The pharmaceutical formulation of claim 5, wherein the ligand associates with a cell marker or tissue marker selected from the group consisting of proteins, polysaccharides, polypeptides, carbohydrates, and lipids.

11. The pharmaceutical formulation of claim 5, wherein the cell marker or tissue marker comprises one or more molecules expressed on the surfaces of pathological cells.

12. The pharmaceutical formulation of claim 5, wherein the cell marker or tissue marker comprises a cell surface receptor.

13. The pharmaceutical formulation of claim 11, wherein the cell marker or tissue marker comprises a cell surface receptor.

14. The pharmaceutical formulation of claim 5, wherein the tissue marker comprises molecules expressed in the pathological extracellular matrix.

15. The pharmaceutical formulation of claim 5, wherein the tissue marker comprises molecules expressed in a certain combination of cells selected from the group consisting of a cell class, a cell type, an organs or a tissue.

16. The pharmaceutical formulation of claim 15, wherein the combination of cells comprises a cancer.

17. The pharmaceutical formulation of claim 16, wherein the cancer is selected from the group consisting of breast, brain, prostate or lung cancer.

18. The pharmaceutical formulation of claim 15, wherein the combination of cells comprises a pathogenic organism.

19. The pharmaceutical formulation of claim 15, wherein the combination of cells comprises an organ.

20. The pharmaceutical formulation of claim 10, wherein the cell marker or tissue marker is selected from the group consisting of surface glycolipid and glycoprotein receptors, integrins, tyrosine kinase and growth factor receptors, cytokine receptors, and G-protein coupled receptors.

21. The pharmaceutical formulation of claim 11, wherein the cell marker or tissue marker is selected from the group consisting of surface glycolipid and glycoprotein receptors, integrins, tyrosine kinase and growth factor receptors, cytokine receptors, and G-protein coupled receptors.

22. The pharmaceutical formulation of claim 20, wherein the receptor is selected from the group consisting of Asialofetuin receptors, asialoglycoprotein receptors, transferrin receptors, folate receptors, Neural Cell Adhesion Molecule (NCAM) receptors, Cluster of Differentiation 36 (CD36) receptor, Cluster of Differentiation 51 (CD51) receptor, Platelet-Derived Growth Factor Receptor (PDGFR), Epidermal Growth Factor Receptor (EGFR), Human Epidermal Growth Factor Receptor 2 (HER2), Human Epidermal Growth Factor Receptor 3 (HER3), and Human Epidermal Growth Factor Receptor 4 (HER4).

23. The pharmaceutical formulation of claim 21, wherein the receptor is selected from the group consisting of Asialofetuin receptors, asialoglycoprotein receptors, transferrin receptors, folate receptors, Neural Cell Adhesion Molecule (NCAM) receptors, Cluster of Differentiation 36 (CD36) receptor, Cluster of Differentiation 51 (CD51) receptor, Platelet-Derived Growth Factor Receptor (PDGFR), Epidermal Growth Factor Receptor (EGFR), Human Epidermal Growth Factor Receptor 2 (HER2), Human Epidermal Growth Factor Receptor 3 (HER3), and Human Epidermal Growth Factor Receptor 4 (HER4).

24. The pharmaceutical formulation of claim 1 or 2, further comprising a matrix material.

25. The pharmaceutical formulation of claim 24, wherein the matrix material is selected from the group consisting of a gel, a film, or a particle.

26. The pharmaceutical formulation of claim 24, wherein the matrix material is selected for topical administration.

27. The pharmaceutical formulation of claim 26, wherein topical administration comprises administration of a gel, film, patch, or liniment.

28. The pharmaceutical formulation of claim 24, wherein the matrix material is biocompatible.

29. The pharmaceutical formulation of claim 24, wherein the matrix material is to be administered internally.

30. The pharmaceutical formulation of claim 29, wherein the matrix material is an injectable material.

31. The pharmaceutical formulation of claim 24, wherein the matrix material disintegrates upon release of a certain quantity of drug.

32. The pharmaceutical formulation of claim 24, wherein the matrix material is in association with an implant.

33. The pharmaceutical formulation of claim 32, wherein the implant releases a certain dose of the drug over a particular period of time.

34. The pharmaceutical formulation of claim 1 or 2, wherein the formulation comprises a water-soluble complex.

35. A method for administering an oligonucleotide drug, said method comprising administering a therapeutically effective amount of the pharmaceutical formulation of claim 1 to an organism in need thereof.

36. A method of delivering a drug to a tissue culture, comprising administering the pharmaceutical formulation according to claim 1.

37. The pharmaceutical formulation of claim 1 or 2, wherein the second nucleotide strand is associated with the first nucleotide strand.

38. The pharmaceutical formulation of claim 37, wherein the association is by hybridization.

39. The pharmaceutical formulation of claim 1 or 2, wherein the covalent bond is reversible.

40. The pharmaceutical formulation of claim 1 or 2, wherein the first single-stranded nucleotide strand is modified to enable conjugation.

41. The pharmaceutical formulation of claim 40, wherein the conjugation is to the polyacetal polymer.

42. The pharmaceutical formulation of claim 2, wherein the first or second nucleotide strand has a sequence that is antisense with respect to a particular gene.

43. The pharmaceutical formulation of claim 37, wherein the second nucleotide strand is associated with the first nucleotide strand by way of an association that is or includes at least one member selected from the group consisting of a van der Waals force, an electrostatic interaction, a hydrogen bond, an ionic bond, a hydrophobic interaction or a donor/acceptor bond.

* * * * *